(12) United States Patent
Harada

(10) Patent No.: US 6,462,538 B2
(45) Date of Patent: Oct. 8, 2002

(54) EDDY CURRENT DETECTION TYPE THIN FILM ELECTRICAL RESISTANCE METER

(75) Inventor: Yoshinori Harada, Kashihara (JP)

(73) Assignee: Sharp Kabushiki Kaisha, Osaka (JP)

(*) Notice: Subject to any disclaimer, the term of this patent is extended or adjusted under 35 U.S.C. 154(b) by 0 days.

(21) Appl. No.: 09/731,102

(22) Filed: Dec. 6, 2000

(65) Prior Publication Data

US 2001/0004210 A1 Jun. 21, 2001

(30) Foreign Application Priority Data

Dec. 10, 1999 (JP) ............................... 11-352202

(51) Int. Cl.$^7$ ...................... H01L 21/66; H01L 21/203; G01R 33/12; G01N 27/72; G01B 7/06
(52) U.S. Cl. ...................... 324/224; 324/222; 324/225; 324/230; 324/234; 324/765; 427/8; 438/10; 438/17
(58) Field of Search ................ 324/207.16, 207.26, 324/222, 224, 225, 230, 234, 236, 708, 765; 427/8–10; 438/10, 11, 17, 18; 216/84, 86

(56) References Cited

U.S. PATENT DOCUMENTS

| | | | | |
|---|---|---|---|---|
| 2,587,631 A | * | 3/1952 | Kuehne | .................. 324/234 X |
| 3,152,303 A | * | 10/1964 | Lary et al. | .............. 324/224 X |
| 4,797,614 A | * | 1/1989 | Nelson | .................... 324/224 X |
| 5,066,912 A | * | 11/1991 | Kwiatkowski | .............. 324/224 |
| 6,072,313 A | * | 6/2000 | Li et al. | ...................... 324/230 |

FOREIGN PATENT DOCUMENTS

| | | | | |
|---|---|---|---|---|
| JP | 59-26055 | * | 2/1984 | .................. 324/224 |
| JP | 59-212759 | * | 12/1984 | .................. 324/224 |
| JP | 5-21382 | | 1/1993 | |
| JP | 6-69310 | | 3/1994 | |

* cited by examiner

*Primary Examiner*—Gerard R. Strecker
(74) *Attorney, Agent, or Firm*—Edwards & Angell, LLP

(57) ABSTRACT

The sheet resistance meter has: a coil which produces a magnetic field; a sensor head provided to enable the magnetic field to induce eddy currents in a thin film formed on a substrate so that the lines of a magnetic force exerted by the magnetic field extend on one side of the substrate; a control device for detecting the sheet resistance of the thin film according to a variation of the magnetic field caused by the eddy currents; a capacitor for achieving resonance with the coil; and a groove section, a primary air port, an auxiliary air port, and a side air port, provided in the sensor head, for controlling the temperature of the coil. The arrangement stabilizes results of the measurement of a sheet resistance by a sheet resistance meter of a one-sided eddy current detection type when it is used continuously.

26 Claims, 26 Drawing Sheets

EDDY CURRENT DETECTION TYPE THIN FILM ELECTRICAL RESISTANCE METER

FIELD OF THE INVENTION

The present invention relates to sheet resistance meters which measure the electrical resistance of a metal or alloy thin film formed by sputtering, vapor deposition, or another thin film formation technique without contacting the thin film, and also to methods of manufacturing electronic components using such meters.

BACKGROUND OF THE INVENTION

A four probe technique is one of conventionally known techniques to measure the electrical resistance of a metal or alloy thin film formed by sputtering, vapor deposition, or another thin film formation technique.

The four probe technique is based on principles explained below in reference to FIG. 23. Four acicular electrodes, which constitute testing probes 52, 53, 54, and 55, are positioned on the surface of a metal film 51 formed on a substrate 50 so that their ends directly contact the surface. Here, the testing probes 52, 53, 54, and 55 are arranged in a straight line and separated from each other by some distance. A potential difference V is measured which develops between the inner testing probes 53 and 54 when an electric current I is passed through the outer testing probes 52 and 55. The resistance R (=V/I) of the metal film 51 is calculated from the measurement. Then, the resistivity ρ is calculated as the resistance R multiplied by the thickness t of the metal film 51 and further by a correction factor F that is a dimensionless value determined from the shape and dimensions of the metal film 51 and the positions of the testing probes 52, 53, 54, 55.

Shortcomings, however, arise from the mechanism of the four probe technique whereby the acicular testing probes 52, 53, 54, and 55 are pressed against the metal film 51 to make direct contact with it: the metal film 51 may be damaged, which leads to production of dust particles. Also, the testing probes 52, 53, 54, and 55 per se are prone to wear due to abrasion and have to be replaced regularly.

Another problem develops with the four probe technique in the presence of vibration or shake, which obstructs the essential direct contact of the testing probes 52, 53, 54, and 55 with the metal film 51 and makes it impossible to perform measurement. A further problem with the four probe technique is related to nothing but the size of a device to execute the method. The device grows too large for various reasons, such as the inclusion of a dedicated clamp stage for measuring, to be readily accommodated in a limited installation space, especially, along with other devices in existing manufacturing lines.

To address these shortcomings, non-contact measurement is available as an alternative to the four probe technique whereby testing probes are brought into direct contact with the target object to measure the resistivity of the semiconductor material.

The technique is known as the double-sided eddy current scheme, which will be detailed here. A metal thin film is formed on a glass substrate, wafer, or other substrate for semiconductor, and the substrate is placed in a magnetic field developed by a coil to which a high frequency power is supplied. Thus, eddy currents are induced in the metal thin film due to electromagnetic effects of the magnetic field. The induced eddy currents will dissipate as Joule heat. The consumption of high frequency electric power by the metal thin film formed on the substrate has a positive correlation with the conductivity of the metal thin film. This fact provides the basis of the double-sided eddy current scheme to calculate the conductivity (the reciprocal of resistivity) of the metal thin film without contacting the thin film.

The double-sided eddy current scheme is unique over the four probe technique in that the resistivity of the metal thin film is can be calculated and evaluated without direct contact. Therefore, with the double-sided eddy current scheme, it is ensured that the metal thin film on the substrate is not damaged by direct contact, pollutants, or exertion of force in the finishing process of ICs, liquid crystal panels, and other semiconductor products.

Now, the double-sided eddy current scheme will be described by way of an example. First, as shown in FIG. 24, a high frequency electric power is supplied to a coil 62b wound around a C-shaped ferrite core 62. The ferrite core 62 has two end parts 62a which are positioned opposite to each other and separated by a 1- to 4-mm gap 61.

When a wafer 63 is inserted in the gap 61, eddy currents are induced in the metal thin film on the wafer 63 due to the high frequencies. Since the induced eddy currents dissipate as Joule heat, the supplied high frequency electric power is partly consumed by the metal thin film on the wafer 63. The consumption has a positive correlation with the conductivity of the metal thin film on the wafer 63. In the double-sided eddy current scheme, the resistivity of the metal thin film on the wafer 63 is measured without contacting the metal thin film based on the ratio of the consumed power.

The double-sided eddy current scheme has been applied in recent development of resistance meters which are intended for use in small sheet resistance monitors to control quality of semiconductors in their manufacturing process. For example, Japanese Laid-Open Patent Application No. 6-69310/1994 (Tokukaihei 6-69310; published on Mar. 11, 1994) discloses a wafer probing system whereby a resistance meter is disposed in the loader section and positioned parallel to the direction in which a transport robot moves so that the resistivity of the wafer can be measured using the resistance meter while the wafer is being transported. The laid-open patent application does not explicitly describe that the resistance meter is based on the double-sided eddy current scheme whereby the resistivity is measured without direct contact. It is inferred from the attached drawings, however, that the invention may be reduced to practice using either a contact-type resistance meter based on, for example, the four probe technique or one based on the double-sided eddy current scheme.

In this measuring system, there is provided an operation flow where either the robot is temporarily halted to measure resistivity or the wafer is inserted into, or transported through, the resistance meter, to measure the resistivity while the wafer is moving.

However, in this prior art system, the resistance meter is lacking in adequate sensitivity to be installed in an existing semiconductor manufacturing process and needs a transporter with one or more axes, for example, which makes it difficult to ensure a suitable installation space. The resistance meter is therefore difficult to install in an existing semiconductor manufacturing process.

Japanese Laid-Open Patent Application No. 5-21382/1993 (Tokukaihei 5-21382; published on Jan. 29, 1993) discloses a similar sheet resistance meter of an eddy current detection type and its usage whereby eddy currents are induced in a metal thin film deposited by sputtering, and lines of a magnetic force produced by the eddy currents are detected without contacting the metal thin film to calculate the sheet resistance.

This laid-open patent application discloses a system installed in the sputtering device that is capable of controlling the sheet resistance of a metal thin film deposited on a wafer or another type of substrate by sputtering. The system includes a load lock chamber interconnected with a gate valve of the sputtering device, a transporter which transports a substrate into the load lock chamber, and a resistance meter which measures the sheet resistance of the metal thin film on the substrate transported by the transporter.

However, in the laid-open patent application, the substrate becomes very hot after the thin film is deposited. The sheet resistance meter of an eddy current detection type is critically affected by the heat through resultant expansion of the coil, temperature dependence of the sheet resistance, etc., and gives inconsistent readings. In addition, the installment of the resistance meter inside the load lock chamber makes maintenance work difficult and inefficient. These problems presumably make it difficult to make use of the sheet resistance value obtained from a previously deposited metal thin film in subsequent deposition.

Conceived of to address these problems was the non-contact sheet resistance meter of a one-sided eddy current detection type producing a magnetic field which acts on a test sample, such as a conducting thin film, to induce eddy currents in it, measures variations in the magnetic field due to the eddy currents, and detects the material of the test sample, i.e., properties of the thin film, through measurement of the sheet resistance.

The operating principle is explained below. First, it is well-known that when a coil 71 to which an alternating current is supplied from an alternating current generator 73 is moved close to a coil 72 (see FIG. 25), a voltage develops across the coil 72 due to electromagnetic induction effects and causes an alternating current to flow in the circuit partly constituted by the coil 72, i.e., an ammeter 74 and a load resistance 75.

Similarly, as shown in FIG. 26, when the coil 71 to which an alternating current supplied is moved close to a metal thin film 76 as a conductivity test sample, instead of the coil 72, eddy currents 77 are induced in the metal thin film 76. The impedance of the coil 71 (corresponding to the resistance for a direct current) is in reverse proportion to the amplitudes of the eddy currents 77 which, in turn, are determined by the distance to the target metal thin film 76, the material and dimensions of the metal thin film 76, and other factors. Thus, the impedance of the coil 71 can be measured and evaluated.

The sheet resistance meter of a one-sided eddy current detection type is so adapted to measure the sheet resistance by detecting dissipation (loss) caused by eddy currents based on variations of the impedance and converting the loss to a sheet resistance value. Specifically, the sheet resistance meter detects the energy loss due to eddy currents based on a difference $\Delta V=|V_0-V_1|$, for example, where $V_0$ is a peak voltage when the permanently activated sensor head is in no vicinity of any other object, that is, placed at infinity, and $V_1$ is a voltage when the sensor head is moved to a predetermined distance of the target metal thin film.

A disadvantage of this type of resistance meter is that it needs to produce a strong magnetic force to sufficiently cause the magnetic flux to concentrate and thus make it practically possible to measure the sheet resistance of the metal thin film, because the resistance meter of a one-sided eddy current detection type produces a magnetic force only on side of the metal thin film. Therefore, attempts are made to increase the strength of the magnetic force produced by the coil 71 by, for example, using electric power with a drive frequency as high as a few hundred kilohertz or even higher and increasing in the number of turns in the coil 71.

There are nevertheless still other problems with the sheet resistance meter. Readings on the sheet resistance meter drift over a long period of time, because the coil 71 is made of copper with a temperature coefficient of resistance of 0.0039 (see Table 1) which imparts temperature properties that are far from being satisfactory to the sheet resistance meter. Further, a higher frequency of the electric power supply causes the sheet resistance meter to generate accordingly more heat and makes it even more difficult to produce a stable voltage output over a long period of time.

TABLE 1

Temperature Coefficient of Resistance

| Substance | Coefficient | Substance | Coefficient |
| --- | --- | --- | --- |
| Silver | 0.0038 | Zinc | 0.0037 |
| Copper | 0.0039 | Magnesium | 0.004 |
| Aluminum | 0.0039 | Cesium | 0.0048 |
| Iron | 0.005 | Iridium | 0.0039 |
| Platinum | 0.003 | Osmium | 0.0042 |
| Mercury | 0.0009 | Manganin | $(3{\sim}10) \times 10^{-6}$ |
| Molybdenum | 0.003 | Constantan | $15 \times 10^{-6}$ |
| Tungsten | 0.0045 | Advance | $\approx 0$ |
| Lead | 0.0039 | | |

SUMMARY OF THE INVENTION

The present invention has an objective to present non-contact, high precision sheet resistance meters of an eddy current detection type which can measure resistivity without halting the facilities or transport robots and without changing the flow in the existing semiconductor manufacturing process, and also to present methods of manufacturing electronic components incorporating the sheet resistance meters.

A sheet resistance meter of the present invention, in order to achieve the objectives, includes:

a sensor head including a coil which produces a magnetic field to induce eddy currents in a thin film formed on a substrate, so that lines of a magnetic force exerted by the magnetic field extend on one side of the substrate;

a sheet resistance detecting section, having a resistor for use in voltage detection, for detecting a sheet resistance of the thin film according to a variation of the magnetic field caused by the eddy currents;

a capacitor for achieving resonance with the coil; and a temperature controlling section which controls a temperature of the coil.

With the arrangement, the sensor head is positioned at a predetermined place above one of the sides of the substrate so that the magnetic field produced by the coil reaches that side of the substrate, but does not extend out of the other side, and the lines of a magnetic force exerted by the magnetic field produced by the coil cross the thin film. Therefore, eddy currents are induced in the thin film due to the lines of magnetic force. Further, the provision of the capacitor which achieves resonance with the coil enables the production of a strong magnetic field.

In this arrangement, the eddy currents dissipate as Joule heat, and the impedance of the coil varies according to the eddy current loss. Hence, the voltage across the resistor for use in voltage detection changes depending on the variation of the impedance. The sheet resistance detecting section detects the sheet resistance of the thin film based on the change in the voltage.

Further, in the arrangement, the detection signal produced by the sensor head according to a variation of the magnetic field caused by the eddy currents is transmitted to the sheet resistance detecting section via, for example, a cable. Since a capacitor is provided considering the cable's stray capacitance C, the sheet resistance meter retains good sensitivity over a long time of period and provides stable performance.

Further, in the arrangement, a temperature controlling section is provided to control the temperature of the coil. Therefore, by the temperature controlling section controlling the temperature of the coil at a constant value, for example, temperature fluctuations cause only a restrained drift in voltage values detected by the coil. The sheet resistance meter thereby produces stable results in detection during operation, especially, during continuous operation.

A method of manufacturing an electronic component of the present invention, in order to achieve the objectives, includes the step of forming a thin film on a substrate, using a thin film forming device, wherein:
the sheet resistance of the thin film is measured using the sheet resistance meter, and the step of forming a thin film is controlled based on the measurement.

Therefore, in the method, the sheet resistance of a thin film on a substrate can be always detected in a stable manner, using the sheet resistance meter. The thin film forming step can be controlled quickly once an abnormality occurs in the sheet resistance of a formed thin film. Yields are thus improved in the manufacture of electronic components with a gate Ta or other thin films.

For a fuller understanding of the nature and advantages of the invention, reference should be made to the following detailed description taken in conjunction with the accompanying drawings.

DESCRIPTION OF THE EMBODIMENTS

FIG. 1 through FIG. 22, the following description will discuss embodiments of the sheet resistance meter of the present invention.

Figure 2:
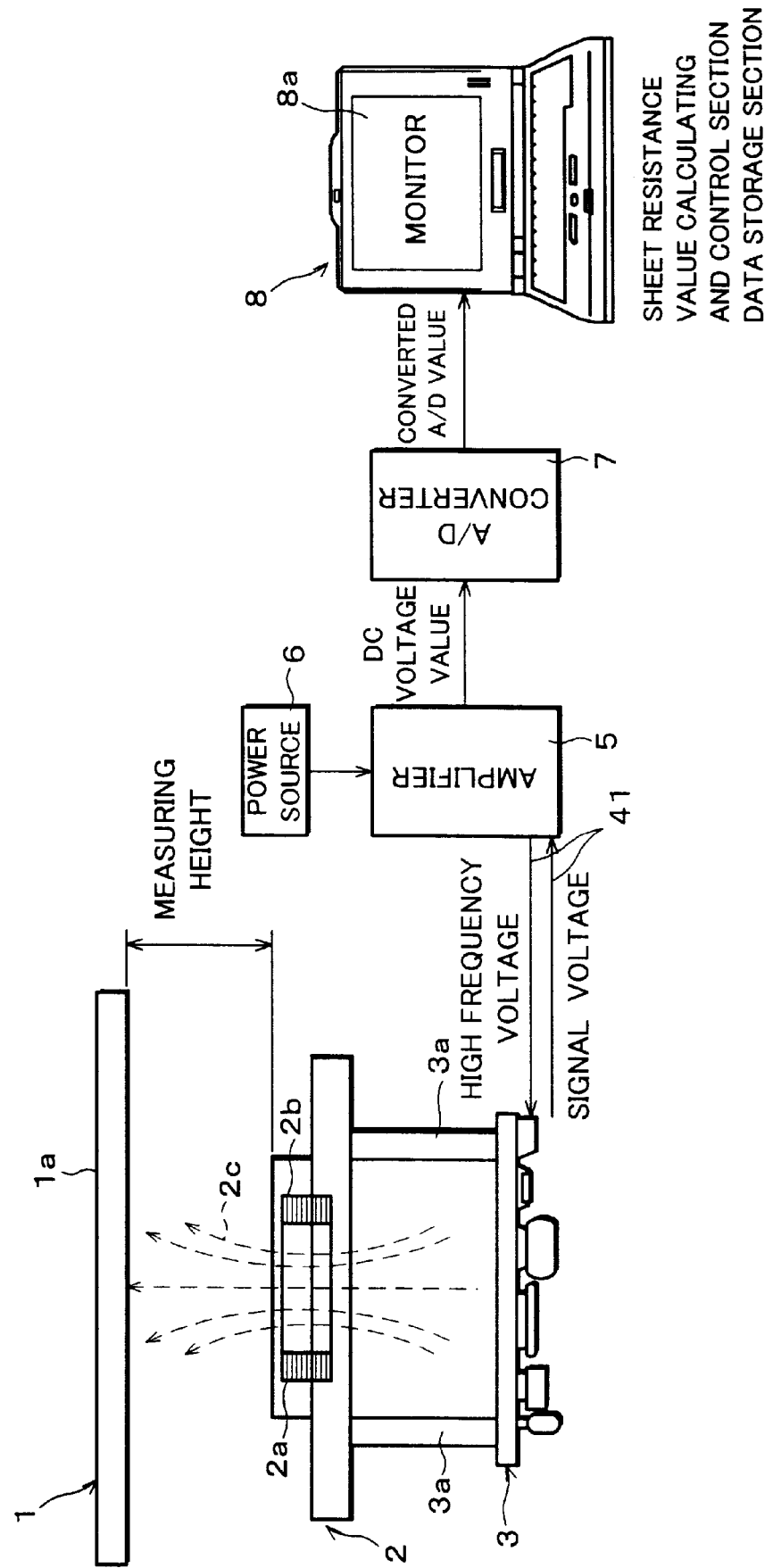
FIG. 2 is a schematic diagram showing a configuration of the sheet resistance meter.

As shown in FIG. 2, the sheet resistance meter has a sensor head 2 to measure the sheet resistance of a thin film 1a, such as a gate Ta thin film. The thin film 1a is formed on the surface of a semiconductor wafer 1 which serves as a substrate. The sensor head 2 includes a coil 2a disposed opposite to the thin film 1a to produce a magnetic field from a high frequency electric power. The coil 2a is toroidal and has no core. The sheet resistance meter also includes an amplifier (sheet resistance detecting section) 5 which supplies a high frequency electric power to the sensor head 2 and converts a detection signal from the sensor head 2 to a DC voltage value (detected voltage value) for output.

A power source 6 is also provided to drive the amplifier 5 and to supply the high frequency electric power from the amplifier 5 to the coil 2a.

The sensor head 2 is housed in a cylindrical container (main body) 2b with a bottom and a lid. The container 2b is made of a non-magnetic substance. Its lid is shaped like a disk and made of a non-magnetic substance. The lid is freely attachable to, and detachable from, the container 2b. Examples of non-magnetic substances include chloride vinyl resins, MC nylons, and ceramics. An MC nylon container 2b would allow an easy look at the interior, because MC nylon is transparent.

Thus, the sensor head 2 is capable of producing a magnetic field 2c (denoted by dotted lines with arrow heads in FIG. 2) so that the central one of lines of magnetic force representing the magnetic field 2c extends toward the semiconductor wafer 1 and crosses the surfaces of the thin film 1a at right angles, causing the magnetic field 2c to induce eddy currents in the thin film 1a on the semiconductor wafer 1. There is provided only one sensor head 2 in the sheet resistance meter, and it is disposed so as to face one of the surfaces of the semiconductor wafer 1.

In these circumstances, the thin film 1a may be formed on either side of the semiconductor wafer 1, opposite to the sensor head 2 or across the semiconductor wafer 1 from the sensor head 2. If the thin film 1a is formed on a far side of the semiconductor wafer 1 from the sensor head 2, the semiconductor wafer 1 needs to allow a magnetic field to pass through it.

An amplifier circuit substrate (amplifier circuit) 3 is disposed close to the sensor head 2. The amplifier circuit substrate 3 is adapted to amplify a high frequency electric power (input signal) from an amplifier 5 and feed the resultant power to the sensor head 2 and also to amplify a detection signal from the coil 2a and feed the resultant signal to the amplifier 5.

Therefore, the variations of the magnetic field at the coil 2a due to the induction of the eddy current are fed to the amplifier 5 via the amplifier circuit substrate 3. When the semiconductor wafer 1 is positioned at a predetermined distance from the sensor head 2 producing a magnetic field, the variations of the magnetic field produced by the sensor head 2 are converted to detected voltage values representative of eddy current losses and detected by the amplifier 5.

Figure 3:
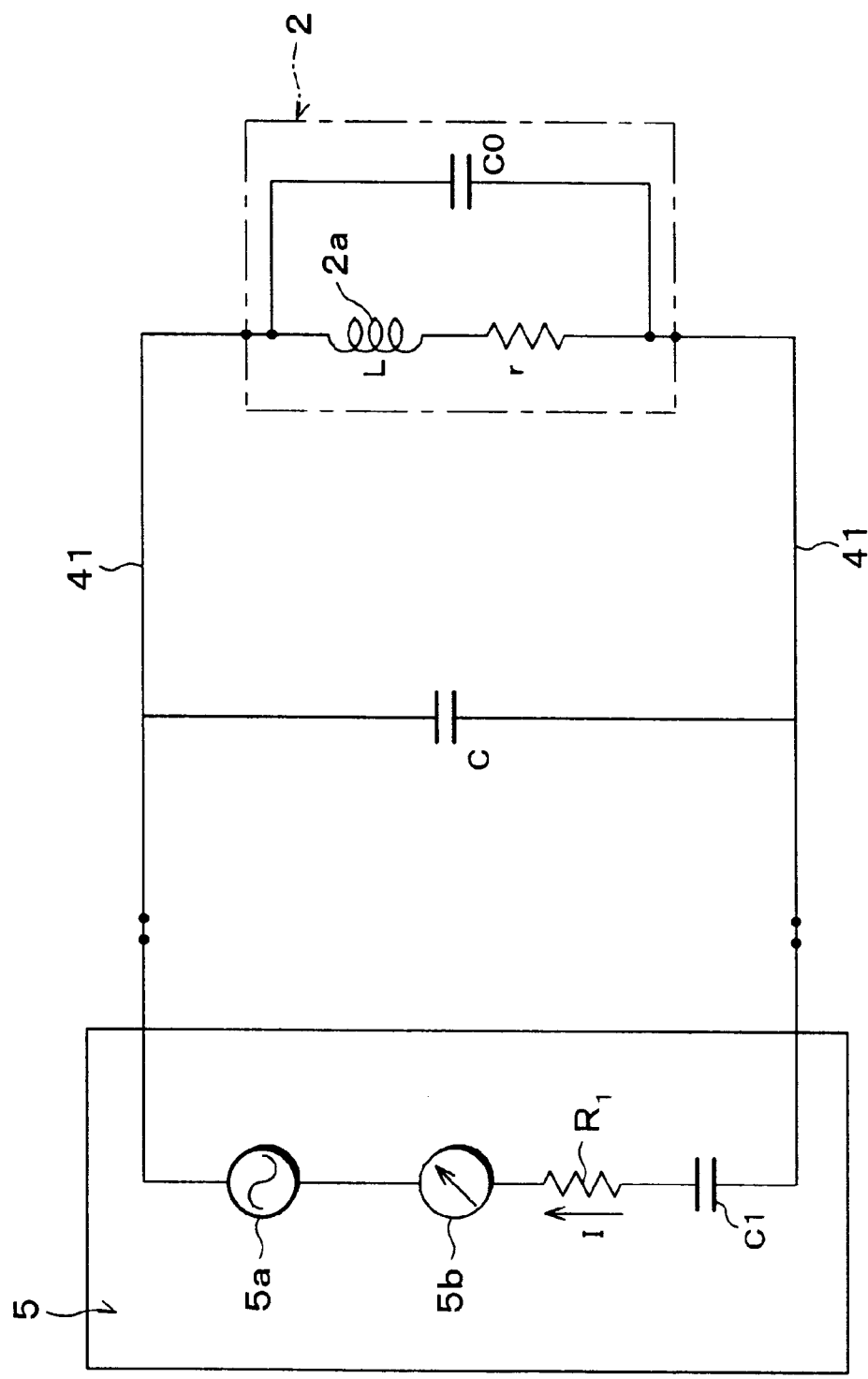
FIG. 3 is a schematic circuit diagram of the sheet resistance meter.
Figure 4:
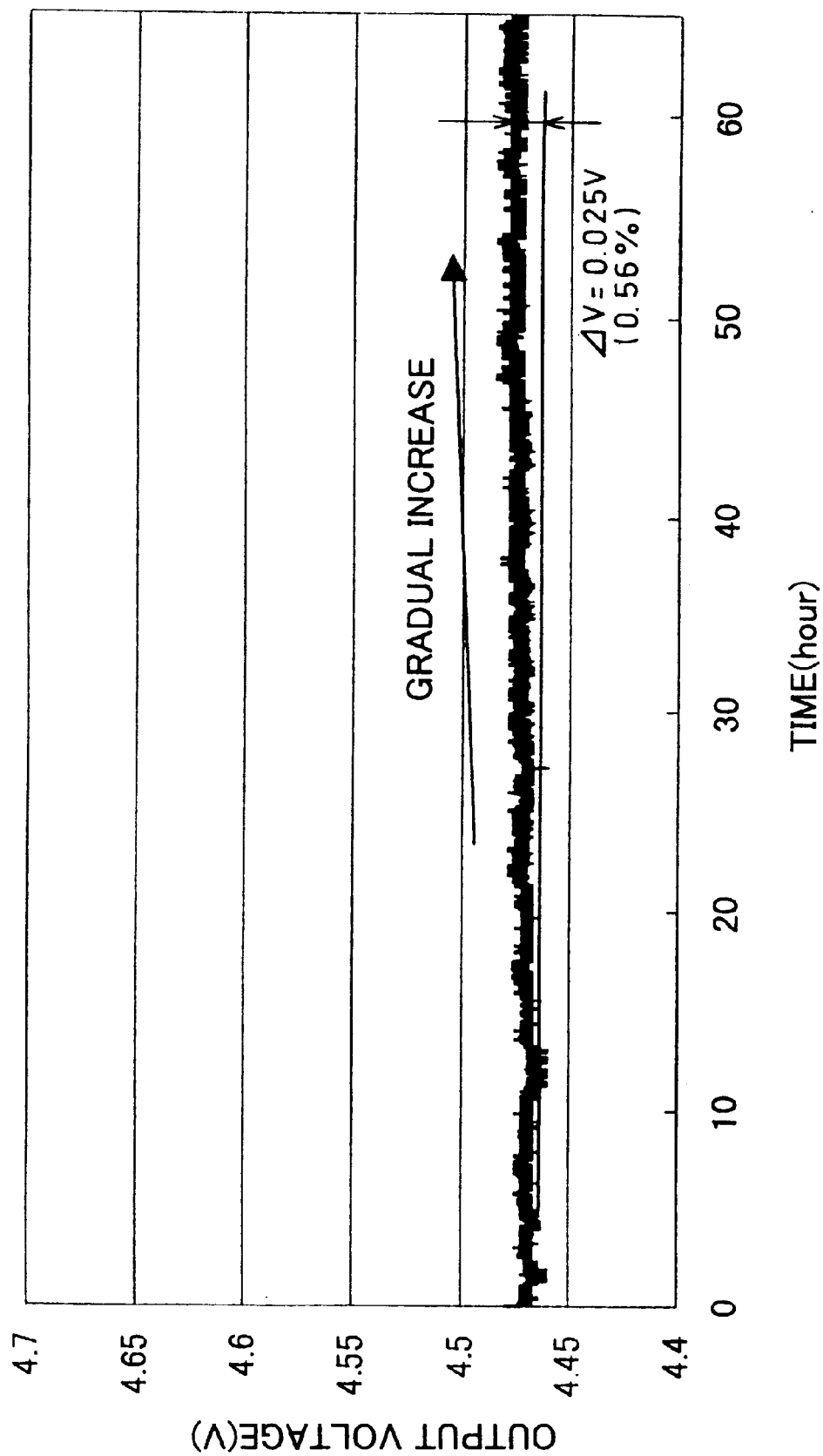
FIG. 4 is a graph showing a temperature-dependent drift of the sheet resistance meter when the container is sealed.
Figure 5:
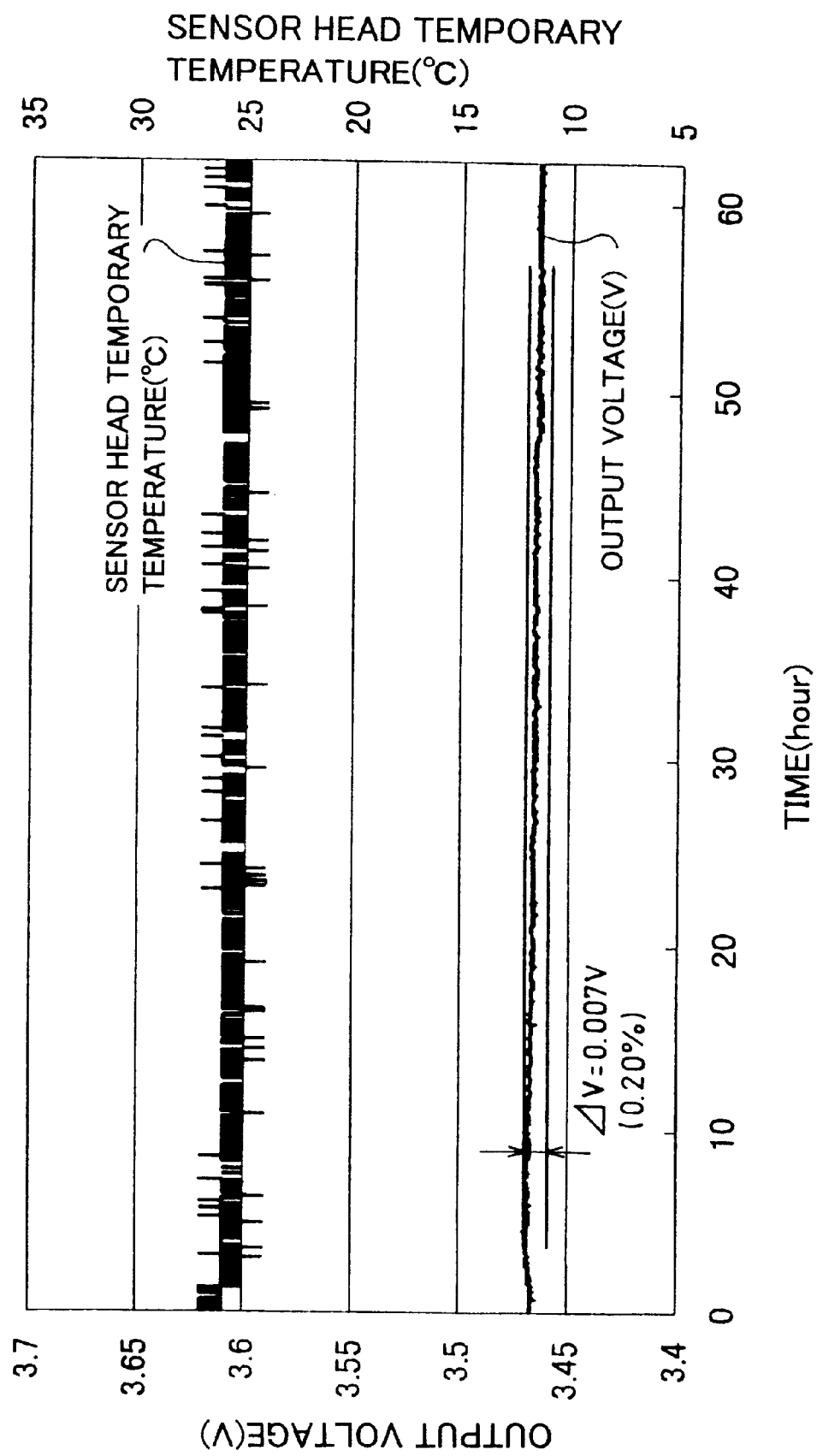
FIG. 5 is a graph showing temperature-dependent variations of the sheet resistance meter when the container is provided with a port, such as a primary port.

FIG. 3 is a schematic circuit diagram of the sheet resistance meter. In the sensor head 2, the inductance L and electrical resistance r of the coil 2a are connected in series, and a stray capacitance C0 of the coil 2a is connected in parallel to the inductance L and electrical resistance r. Cables 41 connecting the amplifier 5 to the coil 2a have a stray capacitance C in parallel to the amplifier 5 and the sensor head 2. In the amplifier 5, an alternating drive voltage generating section 5a, an ammeter 5b, a load R1 for use in detection (resistor for use in voltage detection), and a capacitor C1 for use in sensitivity adjustment are connected in series.

Taking the high frequency of the electric power, the stray capacitance C0 of the coil 2a, and the stray capacitance C of the cable 41 into consideration, the capacitor C1 is specified to keep the coil 2a always in resonance. Always being in resonance, the coil 2a can produce a strong magnetic field which acts on the semiconductor wafer 1, despite that the sensor head 2 is positioned opposite to only one of the sides of the semiconductor wafer 1.

By placing the sensor head 2 so that it faces only one of the sides of the semiconductor wafer 1, the sheet resistance of the thin film 1a formed on the semiconductor wafer 1 becomes measurable from either side of the semiconductor wafer 1, top or bottom, without removing the semiconductor wafer 1 from the manufacture line.

Thus, the sheet resistance of the thin film 1a is now measurable in-line, i.e., without removing the semiconductor wafer 1 from the manufacturing line. This is labor saving in comparison to conventional techniques whereby the substrate must be removed from the manufacturing line to measure the sheet resistance. The sensor head 2 can hence be installed as a part of an existing manufacturing process or device, i.e., can be readily made in-line.

In addition, when the sheet resistance of the thin film 1a formed on the semiconductor wafer 1 is measured, the sensor head 2 is separated from the semiconductor wafer 1 by a predetermined distance and measures the sheet resistance of the thin film 1a formed on the semiconductor wafer 1 without contacting the thin film 1a.

This ensures that the sensor head 2 does not damage the semiconductor wafer 1 or the thin film 1a on the semiconductor wafer 1 through direct contact and at the same time effects the measurement of the sheet resistance of the thin film 1a on the semiconductor wafer 1.

Further, the sheet resistance of the thin film 1a is measurable without removing the semiconductor wafer 1 from the manufacturing line regardless of the material from which the semiconductor wafer 1 is made. This is very helpful when the semiconductor wafer 1 is fabricated from a large piece of glass, since there is no risk of damaging the semiconductor wafer 1 or reducing the performance as a result of the removal and transportation of the semiconductor wafer 1 from the manufacturing line. A larger semiconductor wafer, like 680 mm×880 mm, is increasing costly and benefits greatly from the present invention.

In addition, due to the inclusion of such a sheet resistance meter, the existing manufacturing line is now capable of forming the thin film 1a on the semiconductor wafer 1 with good stability, and no new manufacturing line needs to be separately designed to measure the sheet resistance.

Figure 1A:
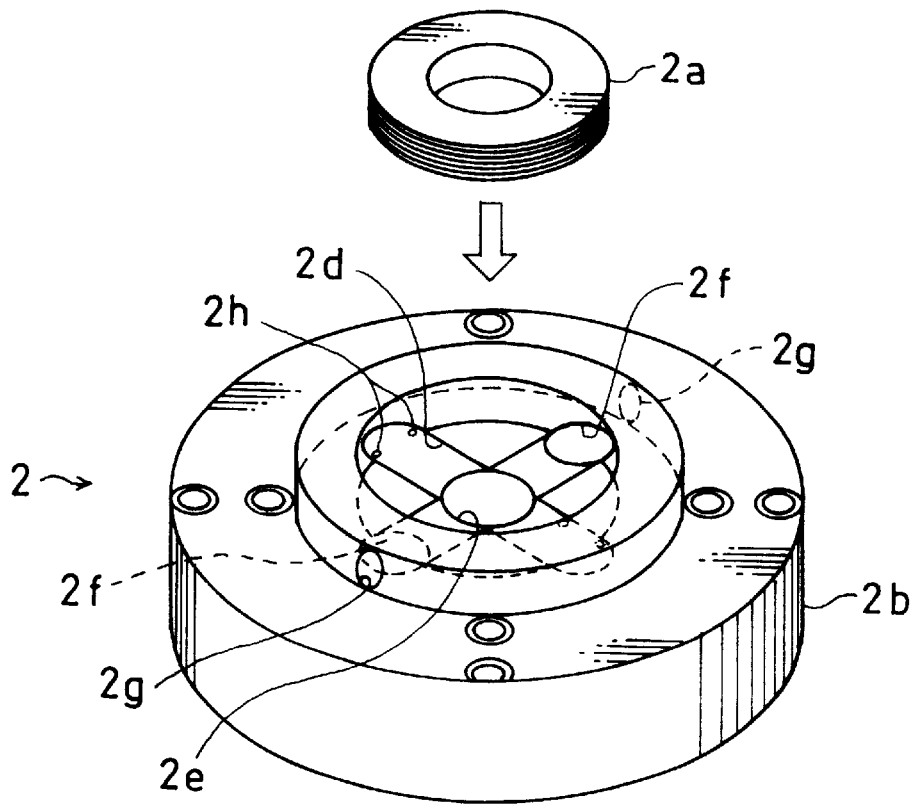
FIGS. 1(a) and 1(b) illustrate a sensor head in a sheet resistance meter of the present invention, FIG. 1(a) being a perspective view showing assembly of a container for the sensor head and a coil housed in the container, and FIG. 1(b) being a perspective view showing a primary air port, auxiliary air ports, side air ports, and groove section formed in the container.
Figure 1B:
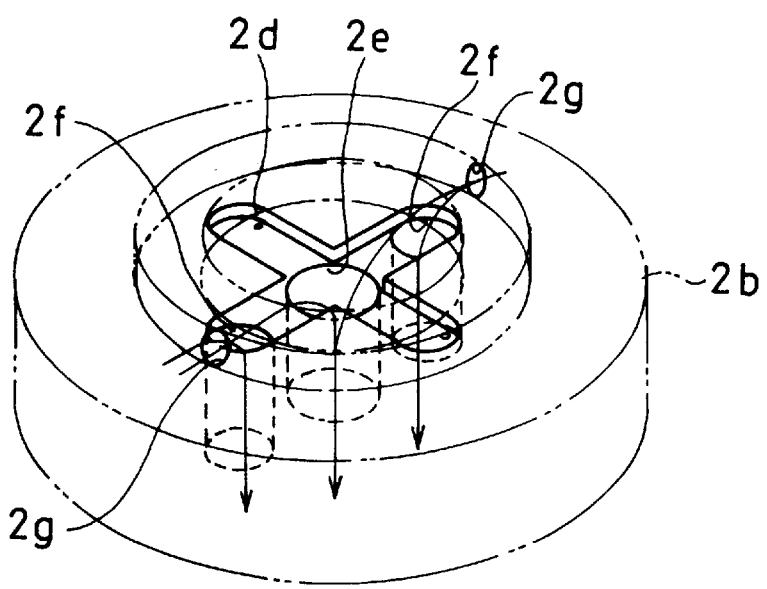

The sheet resistance meter includes at least one of a groove section 2d, a primary air port 2e, a pair of auxiliary air ports 2f, and a pair of side air port 2g, as shown in FIGS. 1(a) and 1(b), which work as a temperature controlling section that controls the temperature of the coil 2a, particularly, restrains rises of the temperature. The groove section 2d is engraved to form a cross at the bottom of the container 2b, and its center is right on the central axis of the container 2b.

The primary air port 2e is cylindrical and shares a common central axis with the container 2b, forming an external passage through the container 2b. The auxiliary air ports 2f are cylindrical and are disposed at the respective ends of the groove section 2d so that they extend parallel to the central axis of the container 2b and symmetric with respect to the primary air port 2e, forming an external passage through the container 2b.

The side air ports 2g are cylindrical and disposed near the respective auxiliary air ports 2f on the side of the container 2b so that the central axis of the side air ports 2g are perpendicular to the central axis of the container 2b, forming an external passage through the container 2b. Connecting holes 2h which provide connection to the coil 2a are bored at the ends of the groove section 2d at which no auxiliary air ports 2f are provided. The shapes of the ports are not limited to the above description: they may be through holes with polygonal cross-sections, for example.

As shown in FIG. 1(b), a gaseous cooling agent, such as air, of a constant temperature enters this container 2b through the side air ports 2g, passes around the coil 2a, flows along the groove section 2d, and exits through the primary air port 2e and the auxiliary air ports 2f. The flow of the cooling agent through these ports keeps the coil 2a at a certain temperature.

Incidentally, since electric power is applied to the coil 2a with a drive frequency as high as a few hundred kilohertz or even higher, if the container 2b is sealed, temperature rises inside the container 2b. This used to cause a drift in voltage values (see FIG. 4).

In contrast, in the present invention, the groove section 2d, the primary air port 2e, the auxiliary air ports 2f, and the side air ports 2g are provided to act as a temperature controlling section to control the temperature of the coil 2a. Through the control of the temperature of the coil 2a at a constant value by means of the primary air port 2e, etc., the coil 2a less likely changes its temperature and produces a restrained drift in its voltage output (see FIG. 5 for the resultant drift). Thus, the sheet resistance meter gives a stable output throughout operation, especially, continuous operation.

The following description will discuss the sheet resistance meter in further detail. As shown in FIG. 2, the amplifier 5 (or more precisely, an OP-amplifier in it) amplifies the detection signal from the sensor head 2 in proportion to the magnitude of the signal, converts the amplified signal to an effective DC voltage value as a detected voltage value, and outputs the resultant DC voltage value to an A/D converter 7. The A/D converter 7 is adapted to convert the detected voltage value (analogue signal) from the amplifier 5 to a digital signal and output the digital signal (A/D converted value) to a control device 8, such as a micro computer. The control device 8 is adapted to calculate the value of the sheet resistance of the thin film 1a formed on the surface of the semiconductor wafer 1 from the digital signal from the A/D converter 7 and stores the obtained sheet resistance in memory.

The control device 8 is adapted to, if the calculated value of the sheet resistance falls out of a predetermined range, determine that the value of the sheet resistance of the thin film 1a formed on the surface of the semiconductor wafer 1 currently undergoing measurement is abnormal, feed an alarm signal representative of the abnormality in the value of the sheet resistance to the CIM (Computer Integrated Manufacturing) process management system (not shown) as well as to a thin film forming device (not shown) which forms a thin film 1a on the surface of the semiconductor wafer 1.

The CIM process management system manages not only the manufacturing process of the semiconductor wafer 1, but manages the whole manufacturing process of the semiconductor device. If the sheet resistance of the thin film 1a on the semiconductor wafer 1 is abnormal, the CIM process management system halts the manufacturing line of the semiconductor device where necessary or take any other steps as required in order to avoid the manufacture of the semiconductor wafer 1 with an abnormal sheet resistance.

The thin film forming device forms the thin film 1a on a glass substrate from which the semiconductor wafer 1 is fabricated by sputtering or vapor deposition. Therefore, if the sheet resistance of the thin film 1a on the semiconductor wafer 1 is abnormal, the thin film forming device immediately halts its operation and stops forming the thin film 1a.

As described above, the control device 8 is adapted to quickly send an alarm signal to the CIM process management system and the thin film forming device according to the procedures above when the value of the sheet resistance of the thin film 1a on the semiconductor wafer 1 is abnormal. Thus, the number of semiconductor wafers 1 manufactured with a deficient thin film 1a is minimized.

The control device 8 includes a monitor 8a, such as a liquid crystal device, to display the value of the sheet resistance of the thin film 1a formed on the surface of the semiconductor wafer 1. Responsible personnel can find out abnormality in the sheet resistance of the thin film 1a on the semiconductor wafer 1 only by monitoring the control device 8 with the monitor 8a.

When abnormality is found in the sheet resistance through the monitoring of the control device 8, the configuration allows the personnel responsible to operate the CIM process management system and the thin film forming device to quickly restore the sheet resistance of the thin film 1a on the semiconductor wafer 1 to a normal state and reduce the number of semiconductor wafers 1 manufactured with a deficient thin film 1a.

The monitor 8a provided to the control device 8 displays a variety of information related to the thin film 1a, including variations of the temperature of the coil (to be described later in detail). The personnel can watch the monitor 8a of the control device 8 and control properties of the thin film 1a on the semiconductor wafer 1 through the settings of various values.

The following description will discuss the sheet resistance meter in terms of its structure in further detail. The amplifier circuit substrate 3 is placed parallel to, and separated by a distance from, the bottom of the container 2b. The front and back sides of the amplifier circuit substrate 3 face the bottom of the sensor head 2 and the bottom of the container 2b respectively. The amplifier circuit substrate 3 is provided with an input-end amplifier circuit (will be described later in detail) which amplifies the high frequency electric power supply to the coil 2a and an output-end amplifier circuit (will be also described later in detail) which amplifies the detection signal representative of the impedance of the coil 2a and supplies the amplified signal for output. A connecting section 3a is disposed at each of the four corners of the amplifier circuit substrate 3 and extends upward to the associated corner of the sensor head 2, so as to keep the sensor head 2 at a distance from, and parallel to, the amplifier circuit substrate 3 and to make electrical connection between them.

The amplifier 5 has a high frequency oscillator circuit (not shown) connected to the coil 2a and a wave detector circuit (not shown) to derive a necessary signal wave (detected voltage value) from the modulated waves from the high frequency oscillator circuit. The high frequency oscillator circuit receives an input of the high frequency electric power which returns from the coil 2a and which varies due to the eddy currents induced in the thin film 1a with respect to the high frequency electric power output to the coil 2a.

The amplitudes of the eddy currents are determined by the distance from the sensor head 2 to the target thin film 1a of which the sheet resistance is measured, the dimensions of the sensor head 2, the material and thickness of the thin film 1a, and other factors. So, the detected value of the high frequency electric power varies according to the magnitudes of the eddy currents.

The high frequency oscillator circuit supplies the variations of the high frequency electric power to the wave detector circuit as a modulated wave, and the wave detector circuit separates a signal wave from the modulated wave and outputs the result as a detection signal. The detection signal is converted to a detected voltage value and supplied to the A/D converter 7.

The semiconductor wafer 1 on which the thin film 1a is formed needs to be removed from the manufacturing line of the semiconductor wafer 1 when the value of the sheet resistance of the thin film 1a grows out of a predetermined range, for example. In this event, the semiconductor wafer 1 of interest is typically removed from the manufacturing line by a robot arm.

To quickly remove from the manufacturing line the semiconductor wafer 1 of which the value of the sheet resistance is evaluated to be deficient, the robot arm should be moved as close as possible to the semiconductor wafer 1 of interest.

With the sheet resistance meter of the present invention, the height of the sensor head 2 can be adjusted, for example, equal to or less than 8 mm. The sheet resistance can be detected and measured using a sensor head 2 mounted to a robot arm.

The following description will now discuss the sheet resistance meter in terms of its installation in a manufacturing line. Here, sensor heads 2 are embedded in a robot arm which is incorporated as a part of an electronic component manufacturing line.

Figure 6:
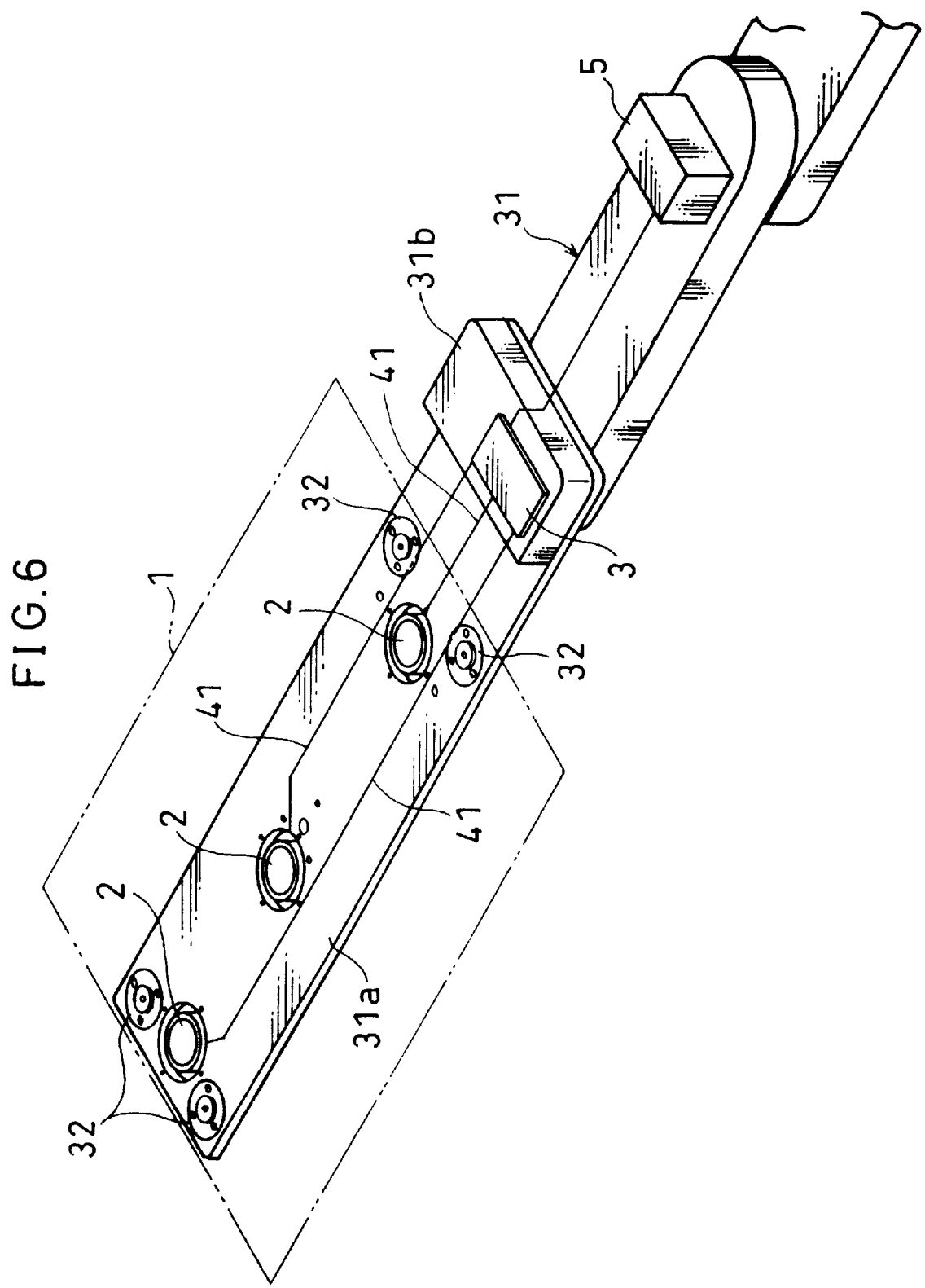
FIG. 6 is a schematic perspective view illustrating the sheet resistance meter being mounted to a robot arm.
Figure 7:
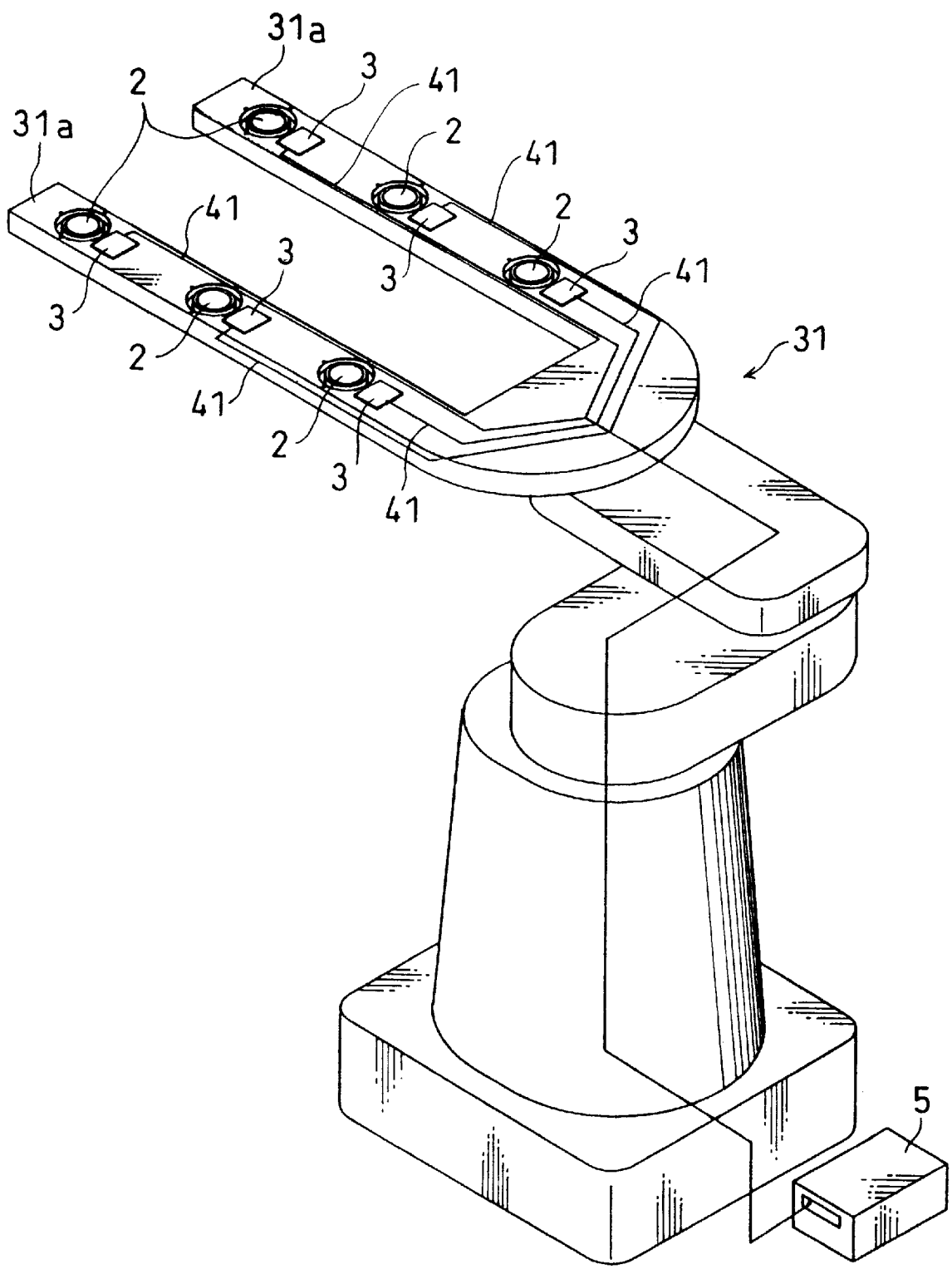
FIG. 7 is a schematic perspective view illustrating the sheet resistance meter being mounted to another kind of robot arm.
Figure 8:
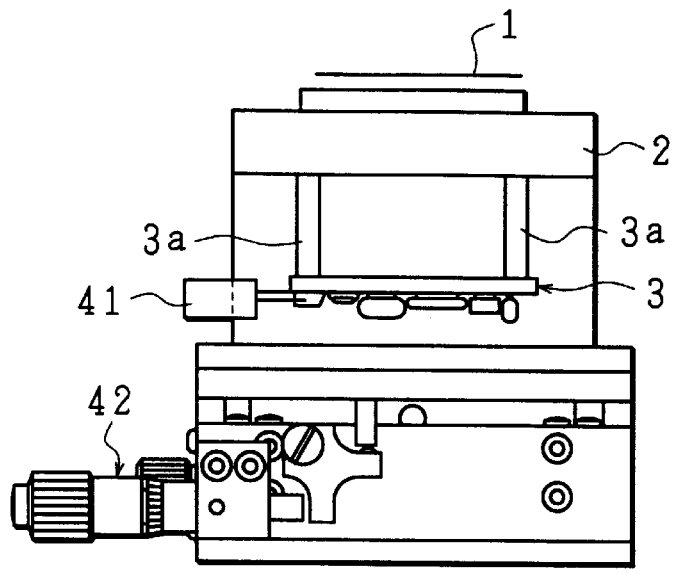
FIGS. 8(a) and 8(b) illustrate the sheet resistance meter mounted to a Z-axis stage, FIG. 8(a) being a front view of the sheet resistance meter, and FIG. 8(b) being a perspective view of the sheet resistance meter.
Figure 8:
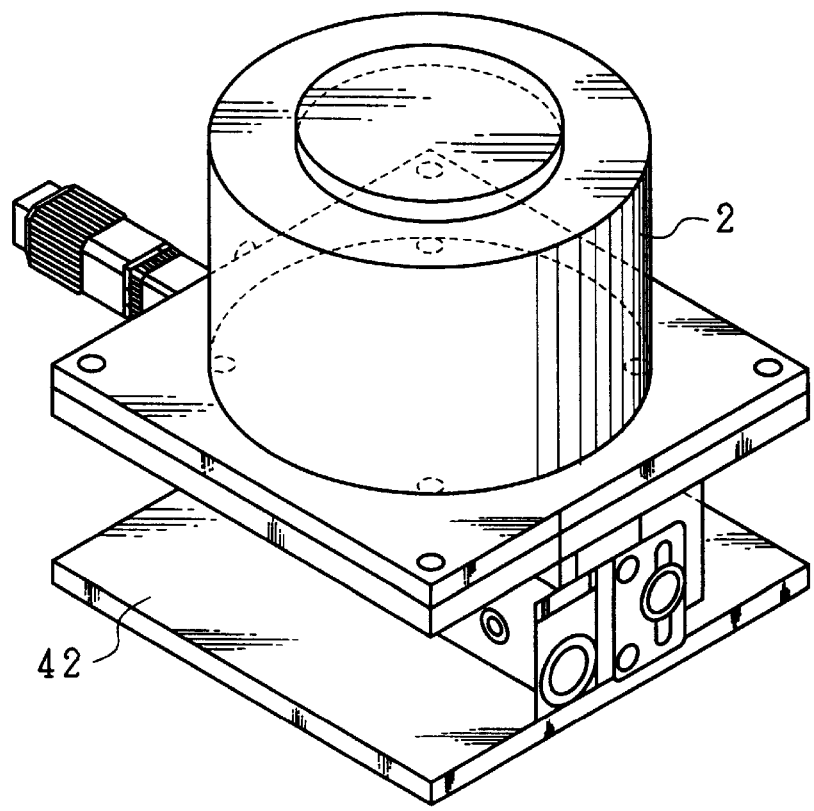

As shown in FIG. 6, the in-line sheet resistance meter has a plurality of sensor heads 2 on which reduction in thickness was attempted as noted previously. The robot arm 31 has, at the end of it, a rectangular plate acting as a hand 31a to hold a semiconductor wafer 1. The sensor heads 2 are embedded in the hand 31a.

The hand 31a is provided with four suction pads 32 to clamp the semiconductor wafer 1 to the top of the hand 31a by air suction, for example. Two of them are located at the distal end of the hand 31a, and the remaining two are located at the proximal end of the hand 31a. The hand 31a may have more or less suction pads 32.

When the semiconductor wafer 1 is clamped to the hand 31a, the distance by which the semiconductor wafer 1 is separated from the hand 31a does not change in the vicinity of the suction pads 32 due to possible bend or other kinds of distortion of the semiconductor wafer 1. Therefore, preferably, the sensor head 2 is placed near the suction pads 32 on the hand 31a. The robot arm 31 has a sensor (not shown) in each suction pad 32 to detect the semiconductor wafer 1 and an amplifier box 31b at the proximal end of the hand 31a for use with the sensors.

The coil 2a measures, for example, 30 mm in outer diameter, 26 mm in inner diameter, and 5 mm in thickness, and has an inductance of, for example, 1.5 mH. In the present embodiment, this specification is equivalent to imparting a thickness (height) of about 7 mm to the sensor head 2 with the thickness of the lid of the container 2b and other dimensions taken into consideration. Being thus fabricated, the sensor head 2 can be embedded in the 8-mm thick robot arm 31. The amplifier circuit substrates 3 provided respectively the sensor heads 2 can be all housed in the amplifier box 31b.

The characteristics of the sensor head 2 in the detection of the values of sheet resistances can be denoted in comparison with those of four probes, for example, based on a sheet-resistance-value correction straight line drawn by plotting the sheet resistance values obtained from measurement of nine different kinds of sample thin films (they differ in material, thickness, etc.) with the four testing probe method and the detected voltage values obtained from measurement of identical samples with the sensor head 2. The sheet-resistance-value correction straight line is given by, for example, Y=1.2126X+4.0103, where Y is the value of a detected voltage, and X is the value of the sheet resistance obtained by the four probe technique.

The value, X, of the sheet resistance becomes obtainable if substituting the value, Y, of a detected voltage, obtained using the sheet resistance meter of an eddy current detection type incorporating the sensor head 2 in accordance with the present embodiment in the above equation representing the sheet-resistance-value correction straight line.

It would be understood from the inclination of the sheet-resistance-value correction straight line that the sheet resistance meter of an eddy current detection type in accordance with the present embodiment is three times as sensitive as a commercially available distance sensor which is applied to a sheet resistance meter of an eddy current detection type. Measurement using a commercially available distance sensor which is applied to a sheet resistance meter of an eddy current detection type yielded a sheet-resistance-value correction straight line with an inclination of 0.4835. In contrast, the same measurement but using the sheet resistance meter in accordance with the present embodiment yielded a sheet-resistance-value correction straight line with an inclination of 1.2126. Therefore, the sensor head 2 in accordance with the present embodiment is capable of detecting the value of the sheet resistance of a thin film which has a higher resistance than a thin film 1a made from Al, Ta, or another low resistance substance.

This way, the sensor head 2 in accordance with the present embodiment is reduced in thickness without a drop in detection sensitivity in comparison to a sensor head 2 fabricated from commercially available components, and therefore can be used embedded in the robot arm 31.

The arrangement detailed so far makes it possible to evaluate the value of the sheet resistance of the thin film 1a formed on the semiconductor wafer 1 when it is moved down along the manufacturing line and passes over the robot arm 31 and to quickly remove the semiconductor wafer 1 with the robot arm 31 if the value of the sheet resistance of the semiconductor wafer 1 is evaluated to be abnormal.

Therefore, the semiconductor wafer 1 with an abnormal sheet resistance value is prevented from being transported to the last stage of the manufacturing line. Thus, only the semiconductor wafers with a normal sheet resistance value are allowed to be transported. As a result, the semiconductor wafer 1 can be evaluated at the stage where the sheet resistance value is detected without separately providing a dedicated stage, which improves efficiency in manufacture.

In the description so far, the sensor heads 2 were mounted to a robot arm 31 of a rectangular plate shape as an example. Alteratively, for example, as FIG. 7, the sensor heads 2 may be disposed on a substantially U-shaped hand 31a.

Now, the advantages of a coreless coil 2a will be explained. Firstly, the value of the sheet resistance no longer drifts, stabilizing the measurement, because without a core in which eddy currents would be induced and cause temperature elevation, the voltage values detected by the coreless coil 2a show improved temperature characteristics. This leads to the omission of correction of the values of the sheet resistances which is otherwise required due to temperature fluctuations and also to improve performance related to the detection of the value of the sheet resistance.

As detailed in the foregoing, there is no need to consider the thickness of a ferrite core in designing a coreless sensor head 2. The sensor head 2 can be therefore reduced in thickness.

The sensor head 2 is fabricated only by winding the coil 2a, which allows more versatile design of the sensor head 2 to be more compatible with the configuration of the existing manufacturing line. The omission of the ferrite core also greatly reduces the manufacture cost of the sensor head 2.

The coil 2a is formed from a single-thread copper wire by winding it. The coil 2a hence increases its AC resistance in response to an increase in the frequency of the electric power applied to it, which entails a skin effect where electric currents flow only along and near the surface of the copper wire. So, the sensor head 2, incorporating the coil 2a formed from a single-thread copper wire by winding it, yields only a limited improvement in sensitivity.

An available alternative to the single-thread copper wire is to use a multistranded wire formed from two or more fine copper threads (hereinafter, will be referred to as Litzendraht wire). In such an event, a skin effect appears in each of the copper threads constituting the Litzendraht wire; however, the Litzendraht wire is formed from multistranded copper threads and, as a whole, carries an electric current quite efficiently. Therefore, the coil 2a, if constituted by a Litzendraht wire, has an improved sensitivity due to a reduced AC resistance and skin effect at high frequencies.

In the above arrangement, if the sensor head 2 includes no core and the coil 2a is formed from a Litzendraht wire by winding it, the sheet resistance can be measured stably at high frequencies, allowing further improvement of sensitivity in detecting the value of the sheet resistance. This enables measurement of the sheet resistance of an ITO (Indium Tin Oxide) sheet and other high resistance thin films.

In the description of the present embodiment so far, a series resonance circuit was used in the coil 2a as an example. An alternative to this is a parallel resonance circuit in which a capacitor C1 for use in sensitivity adjustment is connected in parallel to the coil.

In the sheet resistance meter, the sensor head 2 and the amplifier 5 are electrically connected to each other via the cable 41 formed from, for example, a copper wire. The cable 41 connecting the sensor head 2 to the amplifier 5 creates an additional stray capacitance in the resonant circuit.

Therefore, when the sensor head 2 is separated from the amplifier 5 by an increased distance, the cable 41 connecting the sensor head 2 to the amplifier 5 becomes lengthier, and the stray capacitance of the cable 41 increases. The capacitance of the resonant circuit increases accordingly, causing a reduction in sensitivity in detecting the value of the sheet resistance.

Further, the sensor head 2, even when it is designed with conditions being imposed on the capacitance, still suffers from the adverse effects from the stray capacitance of the cable 41, which causes a problem that sensitivity varies depending upon the length of the cable 41 and sensor heads 2 cannot be manufactured with an identical sensitivity.

Accordingly, in the present embodiment, as shown in FIG. 2, FIG. 8(a), and FIG. 8(b), the amplifier circuit substrate 3 is placed near the sensor heads 2 to reduce the adverse effects from the stray capacitance of the cable 41. Thus, sensor heads 2 can be manufactured at low costs with less susceptibility to adverse effects from a stray capacitance, successfully improving sensitivity in detecting the value of the sheet resistance.

The following description will discuss the amplifier circuit substrate 3 in more detail. The amplifier circuit substrate 3 is disposed in parallel to the sensor head 2 and separated from it by a predetermined distance. A Z-axis stage (adjusting section) 42 is disposed to support the amplifier circuit substrate 3 and the sensor head 2 and move vertically along the Z-axis. The Z-axis stage 42 adjusts the position of the sensor head 2 relative to the semiconductor wafer 1 so that there is a predetermined distance l separating the two from each other.

Figure 9:
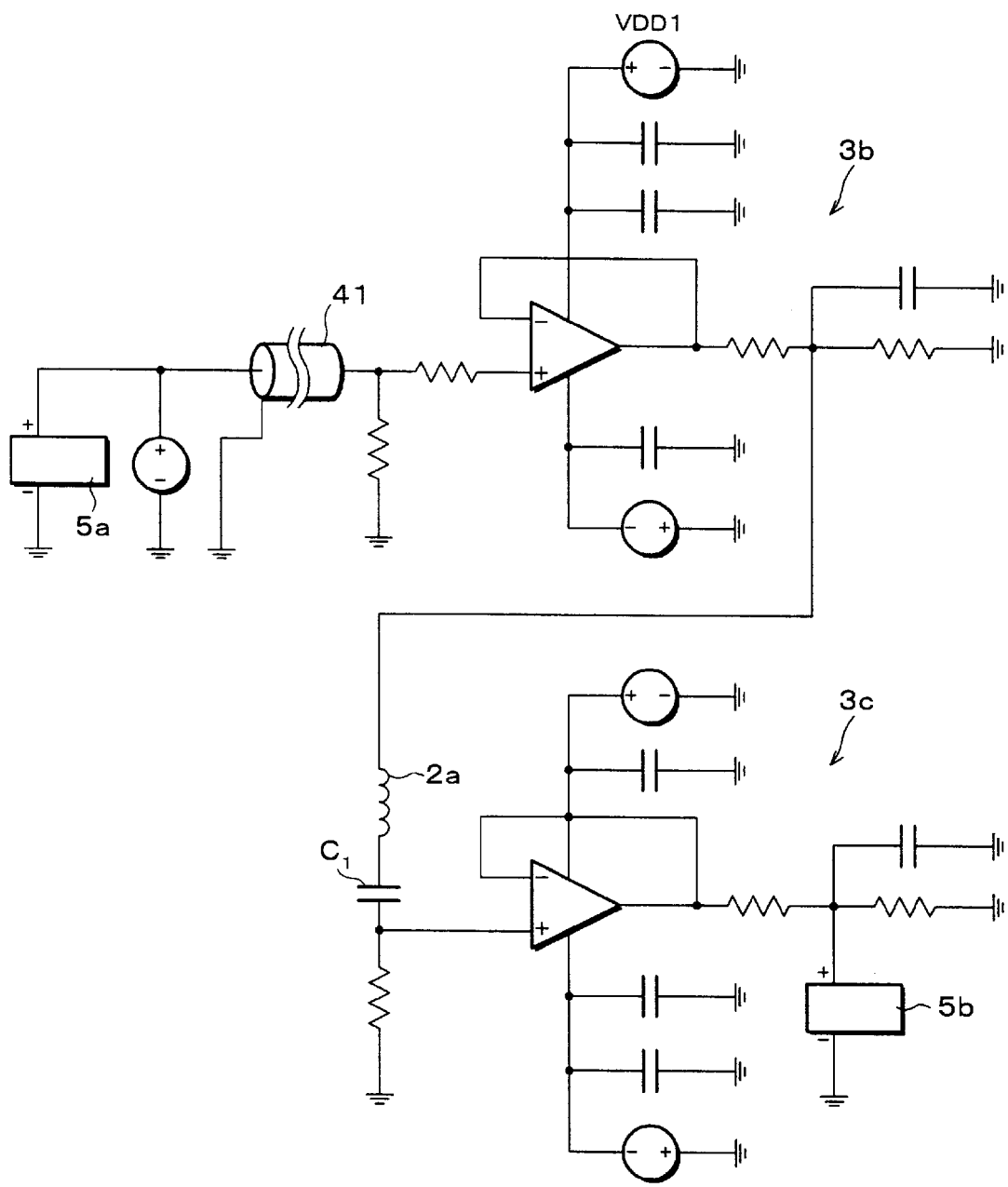
FIG. 9 is a circuit diagram of an amplifier circuit substrate in the sheet resistance meter.
Figure 10:
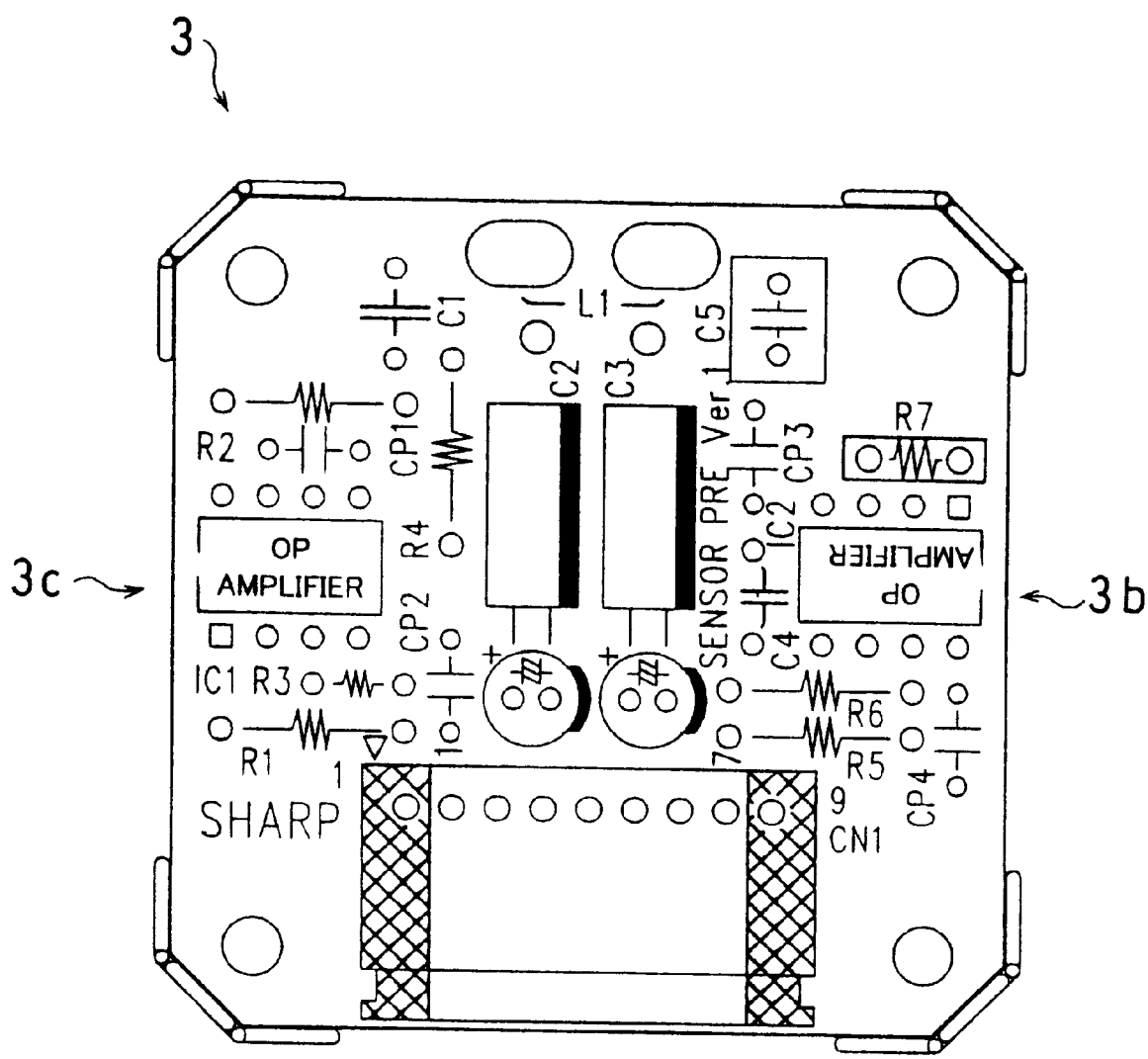
FIG. 10 shows an arrangement of components in the amplifier circuit substrate.
Figure 11:
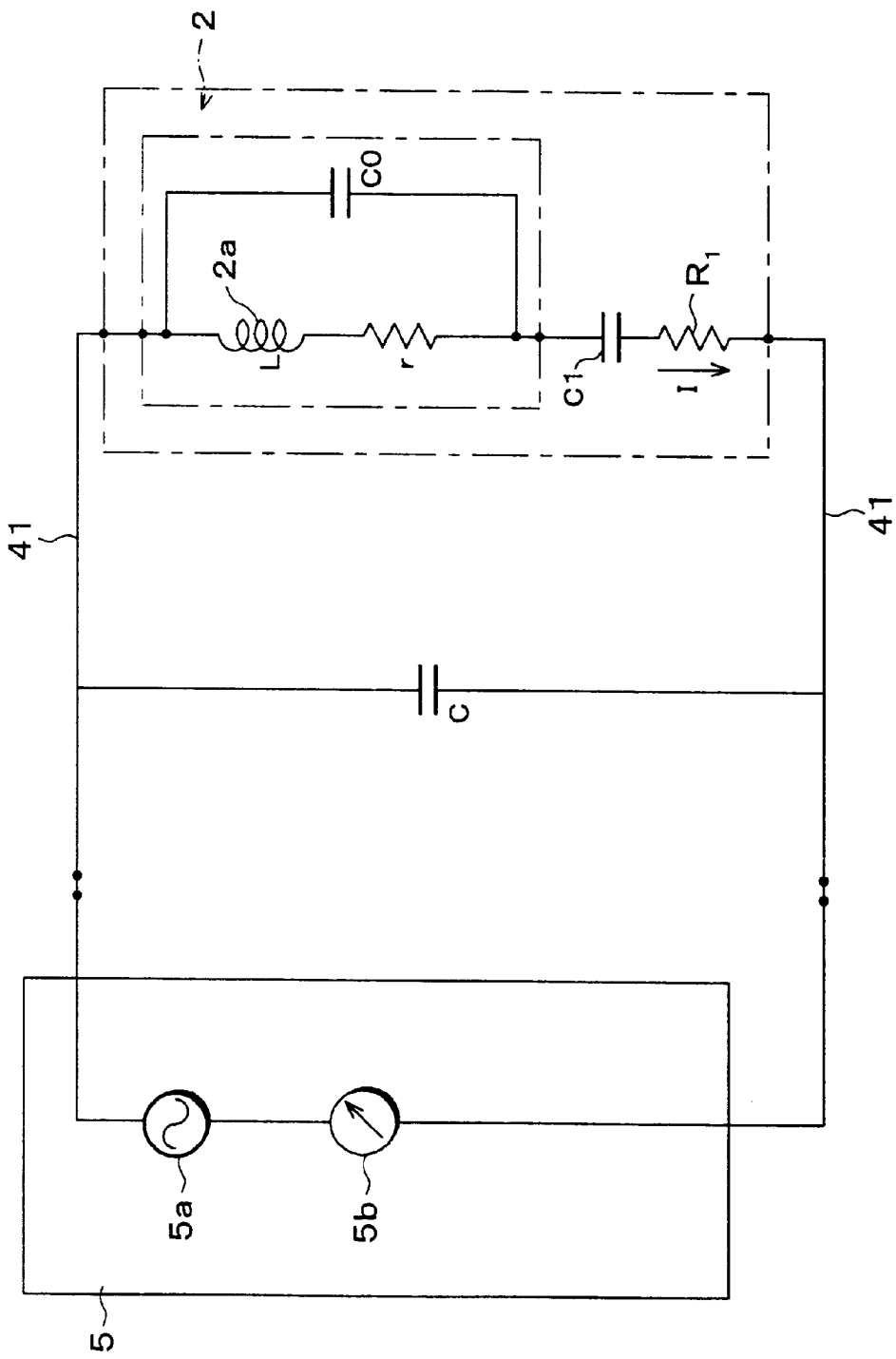
FIG. 11 is a schematic circuit diagram of another sheet resistance meter.
Figure 12:
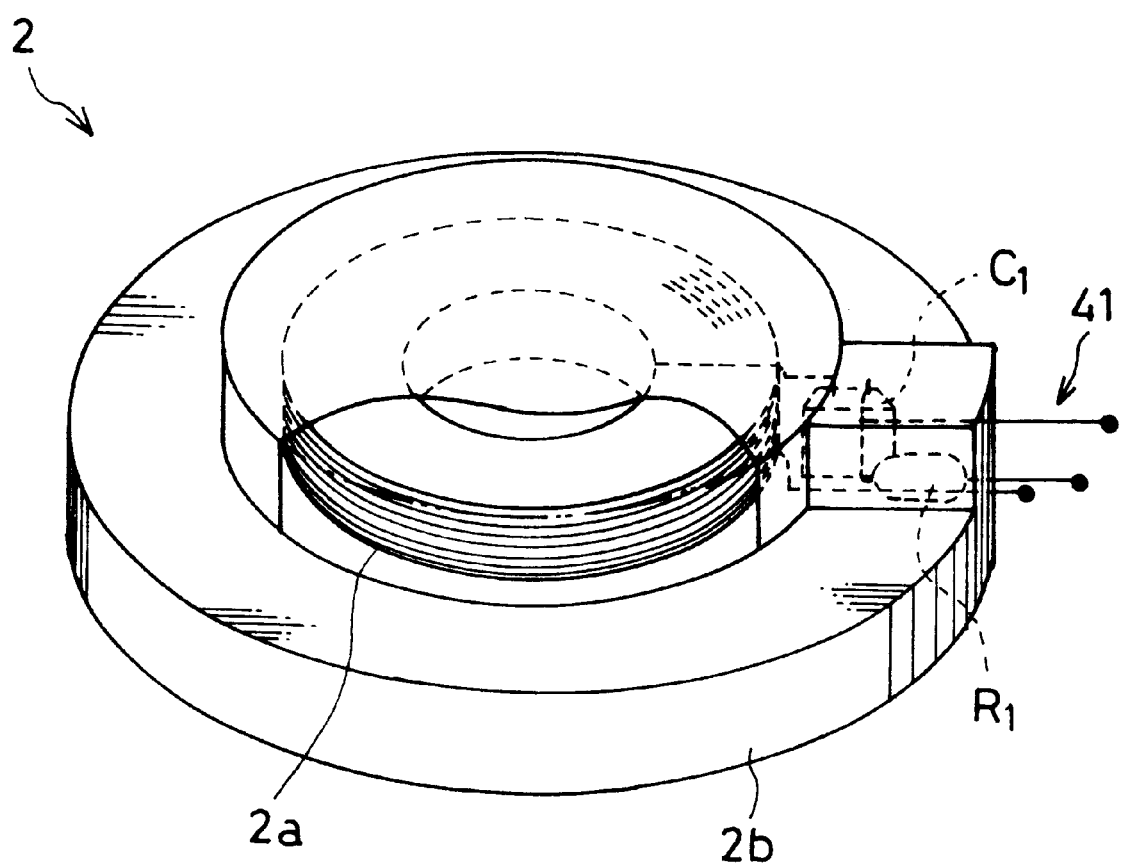
FIG. 12 is a schematic perspective view of the sheet resistance meter.

The amplifier circuit substrate 3, as shown in FIG. 9, includes an input-end amplifier circuit 3b and an output-end amplifier circuit 3c. The input-end amplifier circuit 3b is a unity gain circuit and is coupled to the signal input end of the sensor head 2. The output-end amplifier circuit 3c is a unity gain circuit and is coupled to the signal output end of the sensor head 2.

The input-end amplifier circuit 3b is electrically connected via the cable 41 and the amplifier 5 to the power source supplying a high frequency power, to amplify with an OP-amplifier the high frequency electric power supplied via the cable 41 from an alternative drive voltage source (drive section) in the power source 6 before feeding the electric power to the coil 2a in the sensor head 2.

In contrast, the output-end amplifier circuit 3c is connected at its output end to the voltage signal detecting section acting as the ammeter 5b of the amplifier 5, to amplify with an OP-amplifier the detection signal from the sensor head 2 before feeding the signal to the amplifier 5. The amplifier circuit substrate 3 is electrically connected to the sensor head 2 via a minimum length of the cable 41.

The amplifier circuit substrate 3 solves many problems including insufficient and unstable precision in detection and difficulties in 24-hour long stable measurement of the high resistance of a thin film, such as an ITO film. In the input-end amplifier circuit 3b and output-end amplifier circuit 3c, which are both unity gain circuits, are used a high precision, 16-MHz compatible OP amplifiers whose ratings include, for example, a through rate of 100 V/μs, a bandwidth of 16 MHz at which the OP amplifier operates stably with a gain of 1, a settling period of 350 ms for 0.01% (when driving a parallel load of 100 pF and 500 Ω). To ensure further stability, the input-end amplifier circuit 3b and the output-end amplifier circuit 3c are fabricated, as an example, by effecting art work (package arrangement) on a packaging substrate shown in FIG. 10 with, for example, an allowed variation of the resistance value of 0.1%, a 22 μF (50 V) electrolytic capacitor, a 51-pF (±60 ppm) capacitor C1 for use in sensitivity adjustment, and a 5 mm pitch. According to the art work, the components are arranged symmetric with respect to the central axis in the thickness direction, of the amplifier circuit substrate 3.

As described above, the provision of the amplifier circuit substrate 3 close to the sensor head 2 enables the sensor head 2 to be insusceptible to the stray capacitance of the cable 41 and stably detect the value of the sheet resistance of the thin film 1a.

Further, since the sensor head 2 is insusceptible to the stray capacitance of the cable 41, the limitations on the length of the cable 41 can be loosened. The distance by which the sensor head 2 is separated from the amplifier 5 which applies a high frequency electric power to the sensor head 2 can be determined more freely. Accordingly, the sheet resistance meter becomes more versatile, and the monitor 8a is less limited in terms of its location, facilitating the incorporation of the sheet resistance meter into an existing manufacturing line.

As detailed in the foregoing, when the sensor head 2 is secured to the Z-axis stage 42, the amplifier circuit substrate 3 can be attached to where it can be attached, such as the bottom of the sensor head 2. Further, as detailed in the foregoing, if the sensor head 2 is to be incorporated into the robot arm 31 (see FIG. 6), the amplifier circuit substrate 3 is preferably disposed on the top of the hand 31a of the robot arm 31. However, this does not mean to say that the other possible locations should be excluded: the amplifier circuit substrate 3 may be disposed on the bottom of the hand 31a of the robot arm 31, for example.

In the description so far, the load R1 for use in detection and the capacitor C1 for use in sensitivity adjustment were disposed in the amplifier 5 as an example. Alternatively, for example, as in FIG. 11 and FIG. 12, the load and the capacitor may be disposed in the sensor head 2. In the sensor head 2 shown in FIG. 12, the cable 41 includes three wires. Two of them transmit outgoing detection and drive signals respectively, while the other wire is grounded.

Incidentally, to change the sensitivity of the sheet resistance meter, the capacitor C1 for use in sensitivity adjustment needs to be replaced. Further, the adjustment of sensitivity can be in some cases adversely affected by the fluctuations of the stray capacitance of a cable.

However, the foregoing arrangement restrains adverse effects from the twisting of the cable 41 and external noise and enables stable manufacture of sheet resistance meters, successfully achieving improvements in the adjustment of sensitivity, operation performance, and manufacturability of the sensor head 2.

The control device 8, as a calculation section, is adapted to calculate the sheet resistance according to curvilinear approximation based on the correlation between the value of a detection voltage, which is equivalent to an eddy current loss, and the value of the sheet resistance obtained by a four probe technique.

Figure 13:
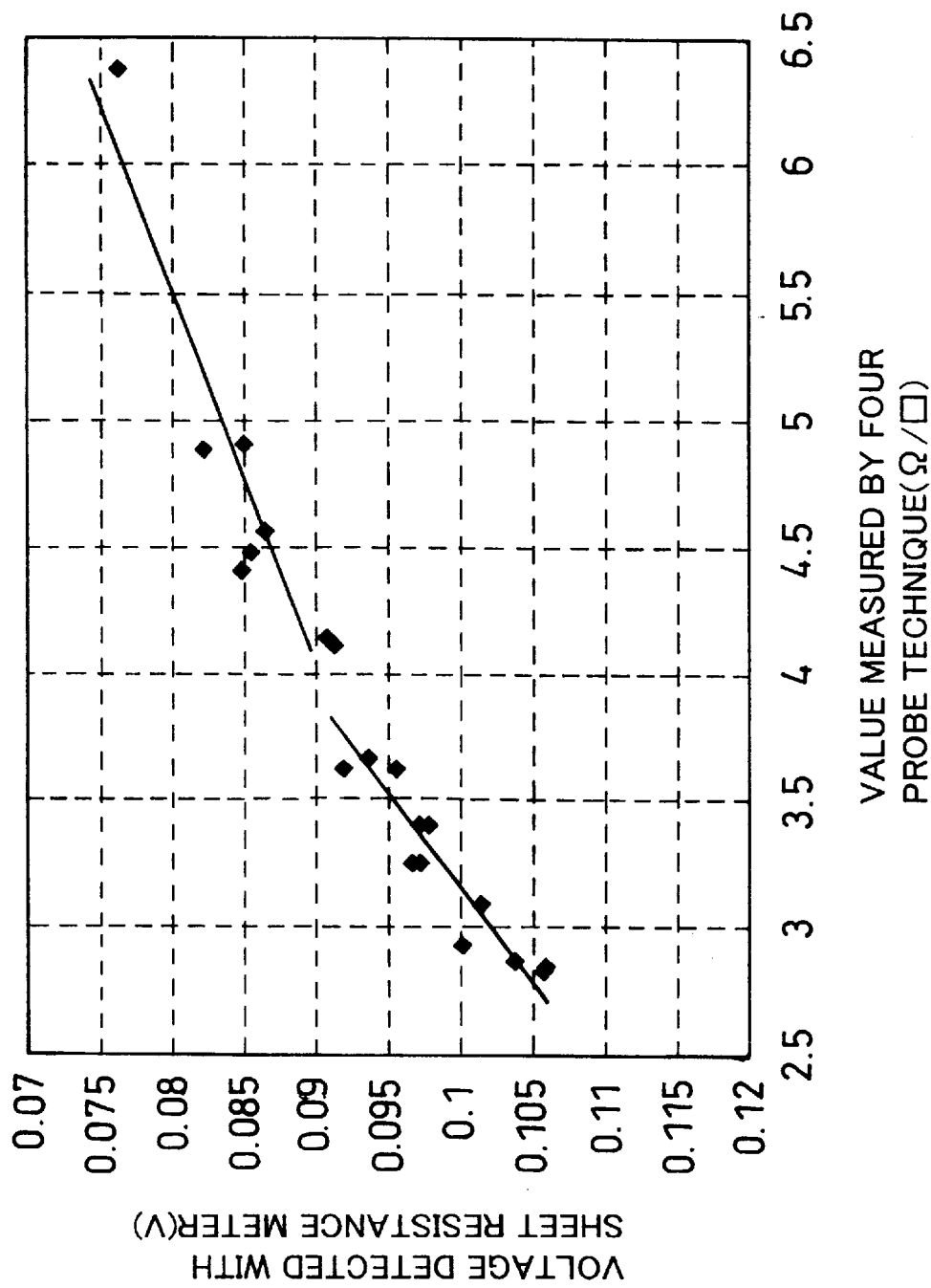
FIG. 13 is a graph showing linear approximation of the correlation between sheet resistance values and detected voltage values obtained using the sheet resistance meter according to a four probe technique.

Conventionally, sensitivity was adjusted where the positive correlation between the value of a detection voltage and the value of the sheet resistance obtained by a four probe technique showed linearity. Therefore, detected resistance values were adjustable only when they are in a limited range. Besides, according to the above conventional method, a different conversion equation was used for each material constituting the thin film 1a, and every time the material of the thin film 1a is changed, performance decreased due to increased workloads in arrangement sample management and an increased number of conversion equations. For example, as shown in FIG. 13, a straight line could be drawn from about 3 Ω/□ to about 3.5 Ω/□ from the correlation data for a Ta gate film in liquid crystal processing. However, as the resistance value exceeds 6 Ω/□, the data does not show linearity any longer, and the precision in detection drops by ±19%.

Figure 14:
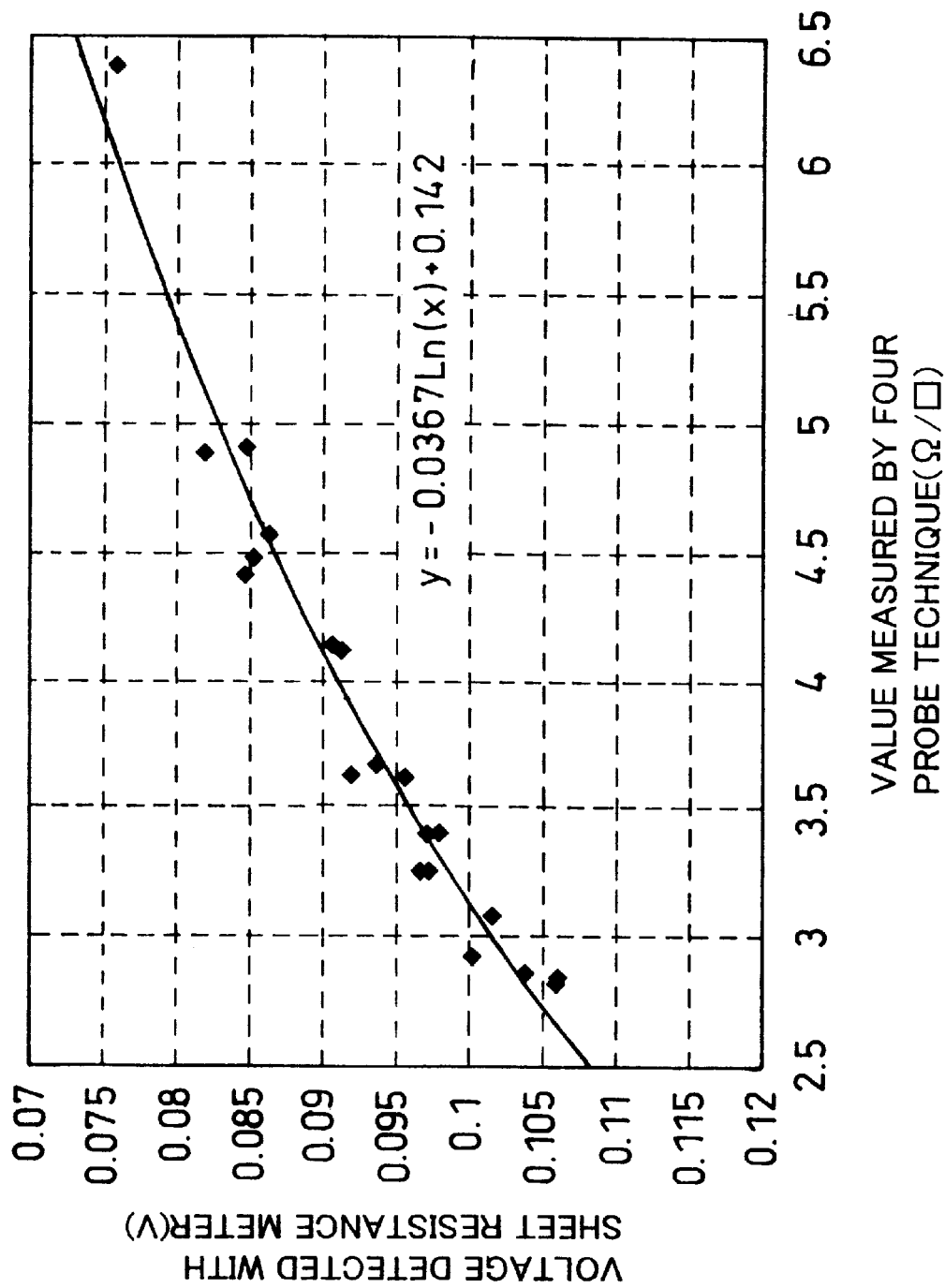
FIG. 14 is a graph showing curvilinear approximation of the correlation between sheet resistance values and detected voltage values obtained using the sheet resistance meter according to a four probe technique.

In contrast, in the present invention, the control device 8 is provided as a calculation section for calculating the correlation between the voltage values equivalent to eddy current losses and the sheet resistance values obtained by a four probe technique based on curvilinear approximation, for example, logarithmic approximation. Accordingly, as shown in FIG. 14, at resistance values exceeding 6 Ω/□, the precision in detection falls within, for example, ±8%, the detection range becomes four times as wide, and the method becomes more adaptable to materials for the thin film 1a.

The sheet resistance meter needs to be adjusted in terms of sensitivity to optimize its output depending on the kind of the thin film 1a. It would be safe to presume that when the sheet resistance meter is positioned close to the object to be measured, the magnetic field applied induces strong eddy currents in the thin film 1a, and the sensitivity is improved.

Figure 15:
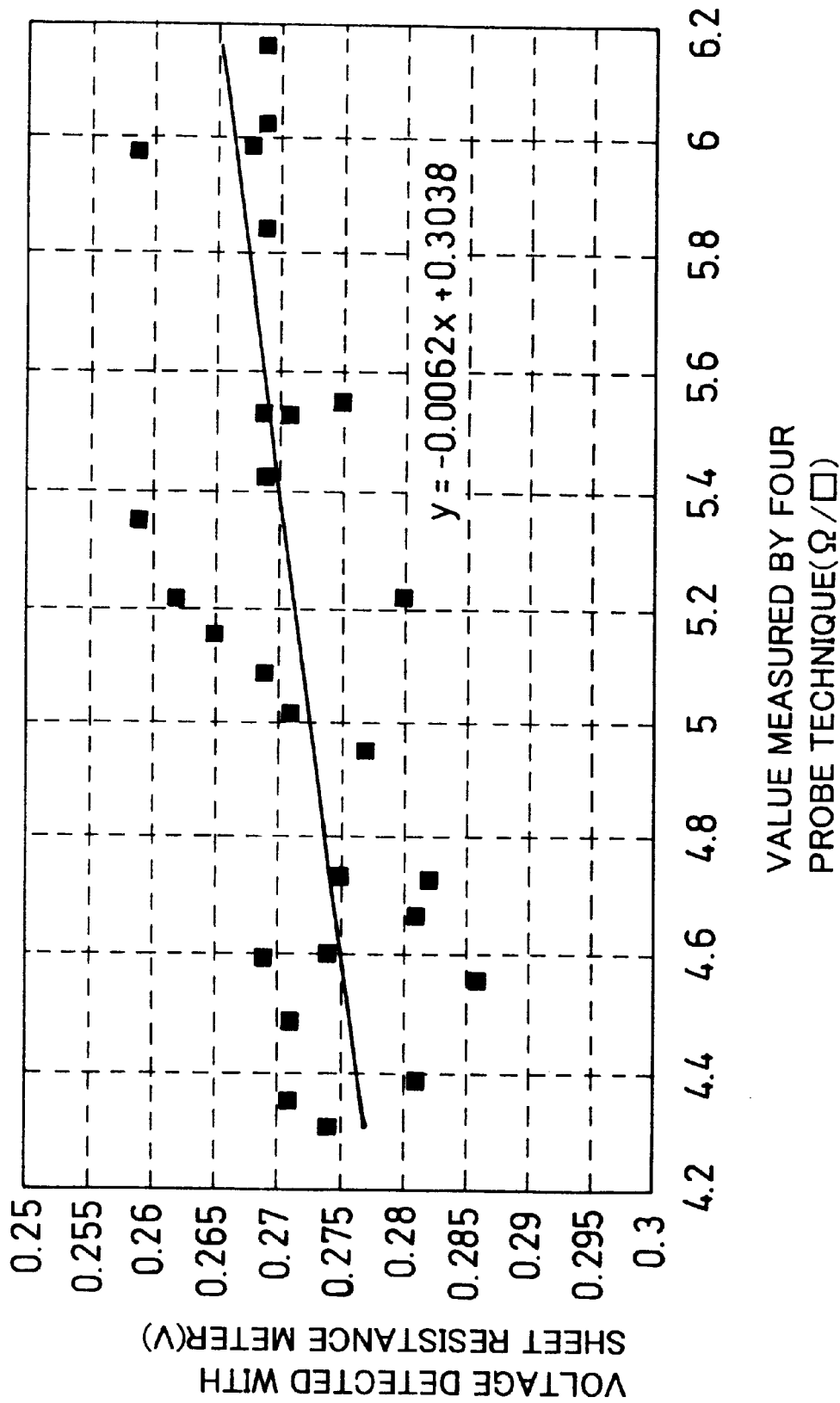
FIG. 15 is a graph showing measurements when the sheet resistance meter is positioned at a distance of 1 mm between the target object and the sheet resistance meter.
Figure 16:
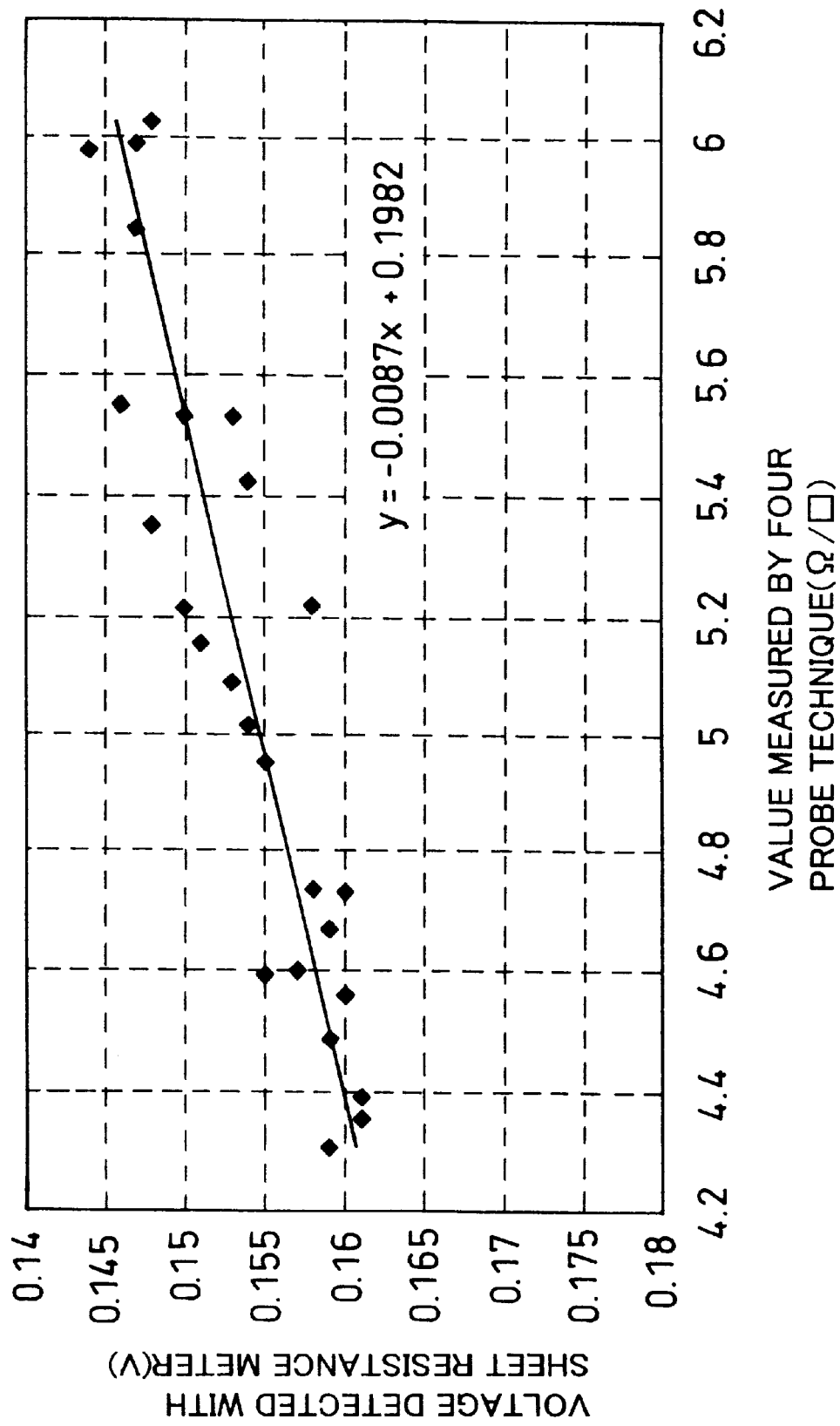
FIG. 16 is a graph showing measurements when the sheet resistance meter is positioned at a distance of 1.8 mm between the above the target object and the sheet resistance meter.

However, for example, when a pure Ta gate film is to be formed as the thin film 1a on the semiconductor wafer 1 in a manufacturing process of liquid crystal panels, as shown in FIG. 15, when the measuring height, that is, the distance by which the sensor head 2 is separated from the thin film 1a, equals 1 mm, results do not show good correlation with the four probe technique. When the measuring height is gradually increased up to 1.8 mm, results show improved correlation with the four probe technique as shown in FIG. 16. From this data, the pure Ta gate film can be measured with good sensitivity when the measuring height is 2 mm.

Therefore, as an adjusting section of the measuring height, the aforementioned Z-axis stage 42 is provided to move the sensor head 2 along the z-axis. By changing the measuring height, conditions can be determined under which results of measurement show an optimum correlation with the four probe technique, sensitivity can be adjusted readily when there is a change in the material or thickness of the thin film 1a.

Figure 17:
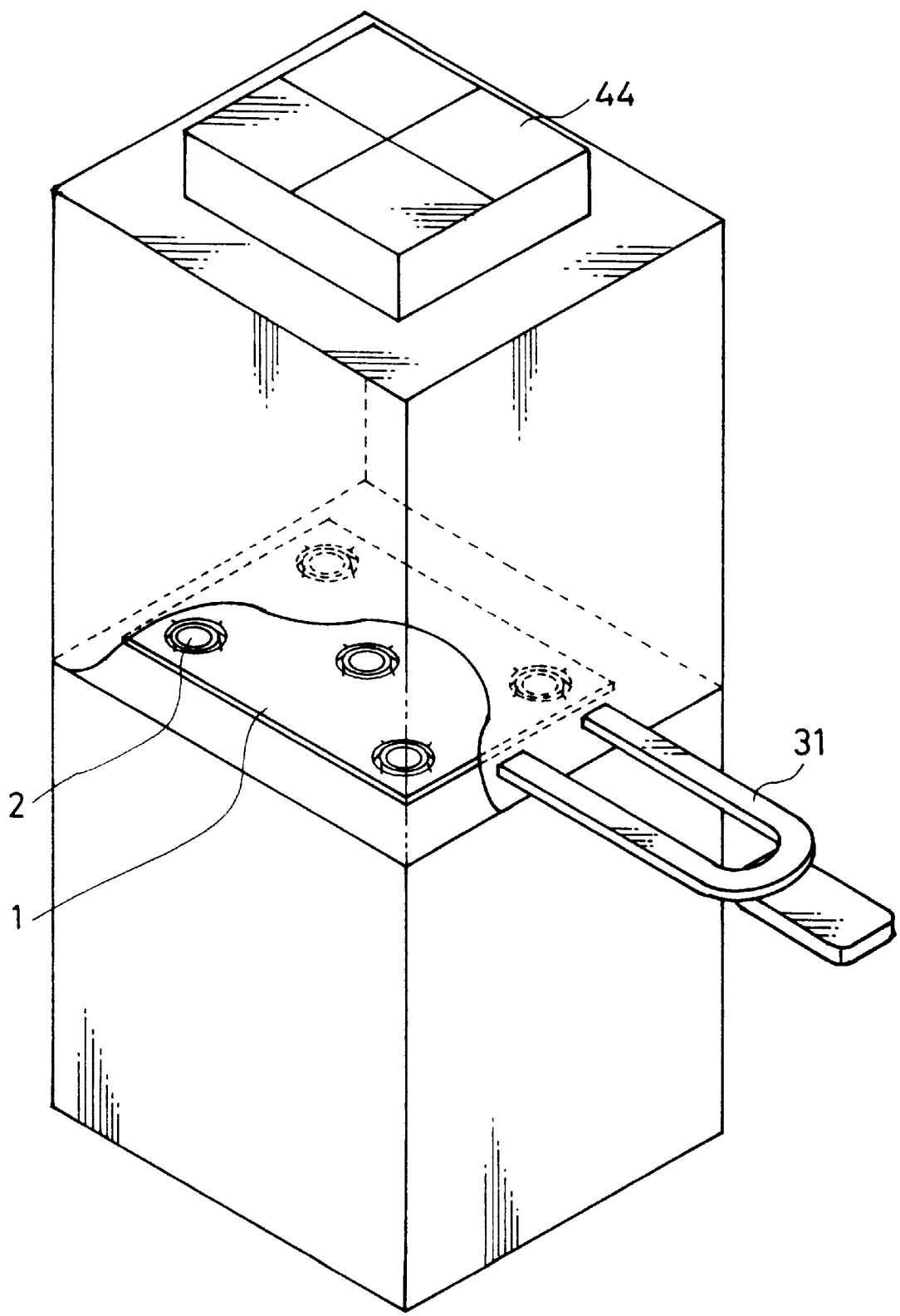
FIG. 17 is a schematic perspective view showing the sheet resistance meter installed in an HEPT.

In the description so far, the primary air port 2e and other air ports were provided as an example of a temperature controlling section. An alternative arrangement is shown in FIG. 17, which is used in a clean room in a liquid crystal or semiconductor process. In the arrangement, an HEPA (temperature monitoring and controlling device which produces a gas flow of constant temperature at a fixed rate) 44 is provided as a temperature controlling section to monitor and control temperature (25±1° C.), and the sensor head 2 is located in the constant gas flow made by the HEPA 44 to produce better results (stability in measurement). The provision of the HEPA 44 is further beneficial in that dust and unwanted particles are prevented from being attracted to the thin film 1a and the sensor head 2, further stabilizing the measurement by the sheet resistance.

Figure 18:
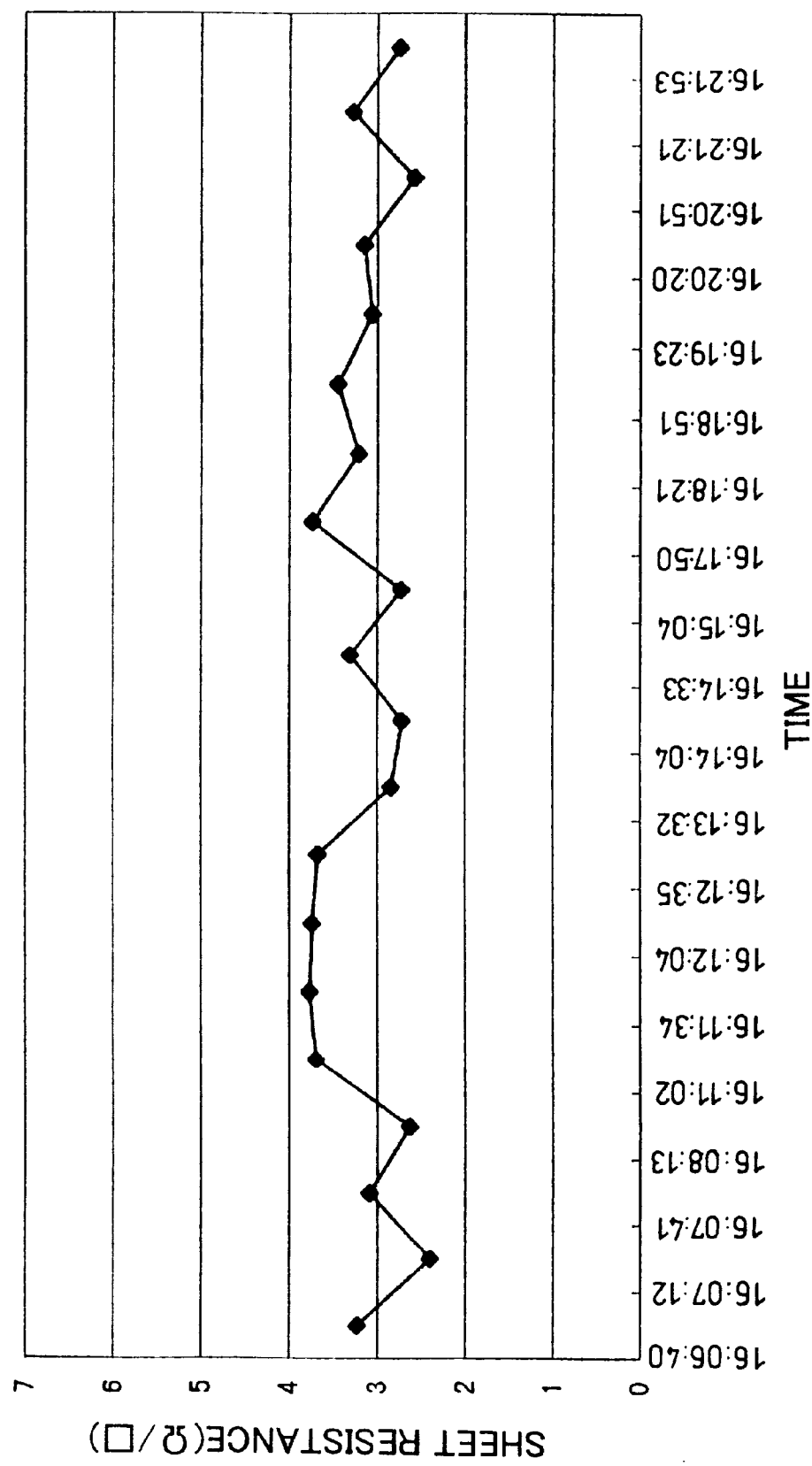
FIG. 18 is a graph showing lot data obtained using the sheet resistance meter, indicating that metal thin films were formed with normal values.

If the sheet resistance meter is installed for every process in an electronic component manufacturing line, any sudden deficiency that occurs to the semiconductor wafer 1 is quickly addressed in the manufacture of the semiconductor wafer 1 with the thin film 1a, which stables the manufacture of electronic components. The sheet resistance of a pure Ta gate film formed on a 360 mm×465 mm liquid crystal substrate (corresponding to the thin film 1a and the semiconductor wafer 1 respectively) was monitored at center of the film over a period of time as an example, and the collected data was analyzed. Results are shown in FIG. 18. It would be understood from the figure that the allowable (acceptable) values of the sheet resistance ranges from 2 Ω/□ to 5 Ω/□, the measurement of the sheet resistance is stable, the measured values of the sheet resistance are confined in a narrow range. Overall, the semiconductor wafer 1 is stably manufactured with a satisfactory thin film 1a.

Figure 19:
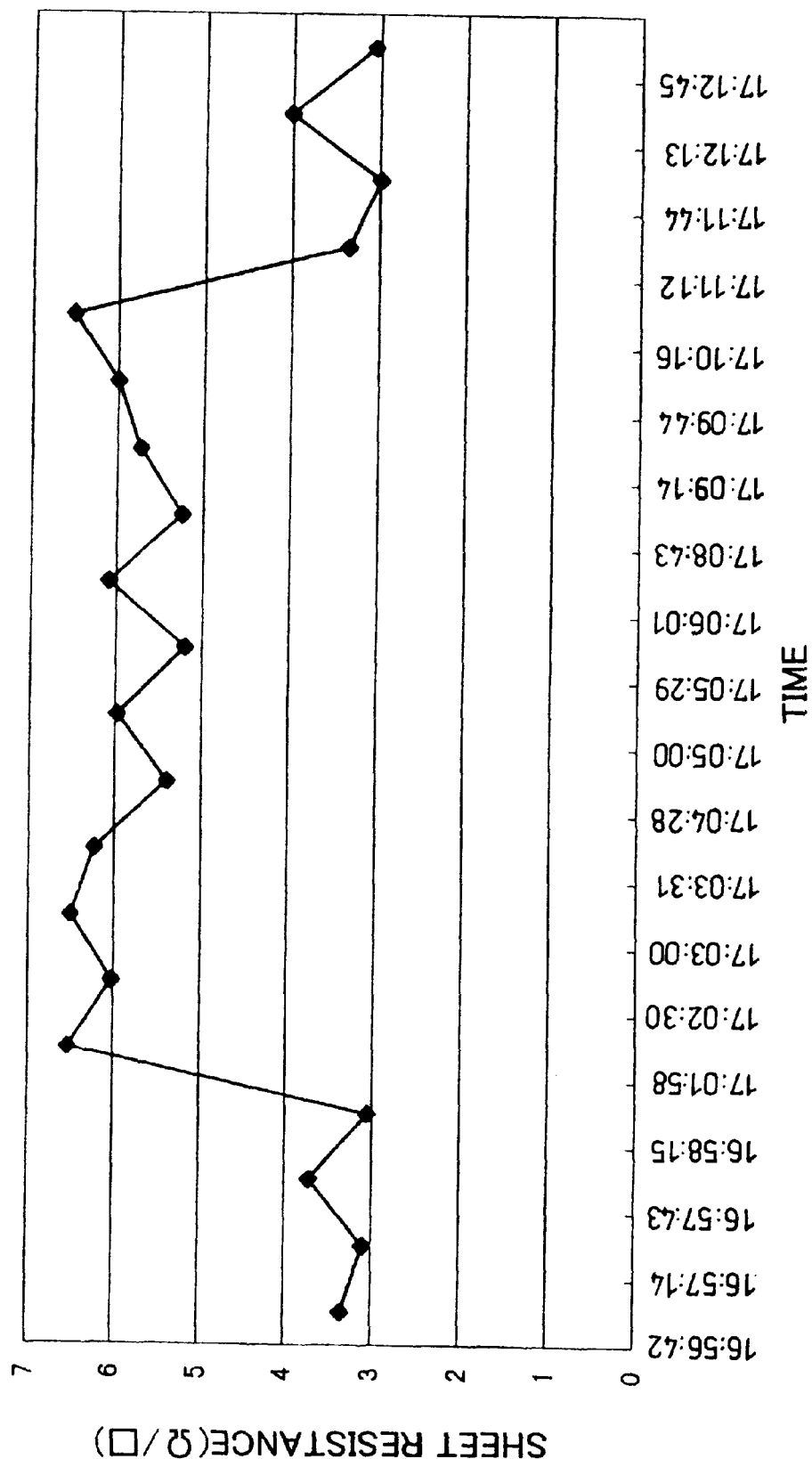
FIG. 19 is a graph showing lot data obtained using the sheet resistance meter, indicating that metal thin films were formed with abnormal values, but they were soon restored to normal values.

In contrast, for example, as shown in FIG. 19, data is representative of occurrence of a sudden deficiency and show that after an abnormality had been detected in the sheet resistance of the pure Ta gate film as a thin film 1a through measurement of the sheet resistance, the film forming conditions were changed to restore the sheet resistance to a normal state, which contributed greatly to the improvement of yields of liquid crystal substrates. For your reference, a cost of about half a million yen is spent for each lot (or twenty liquid crystal substrates) in the manufacturing process up to the formation of the pure Ta gate film.

Incidentally, in single wafer and other types of sputtering devices, the semiconductor wafer 1 becomes as hot as 80° C. when moving out of a gate lock room. The heat adversely affects the measurement of the sheet resistance and therefore makes it difficult for the sheet resistance meter to be installed in the manufacturing line to carry out monitoring of the sheet resistance.

Figure 20:
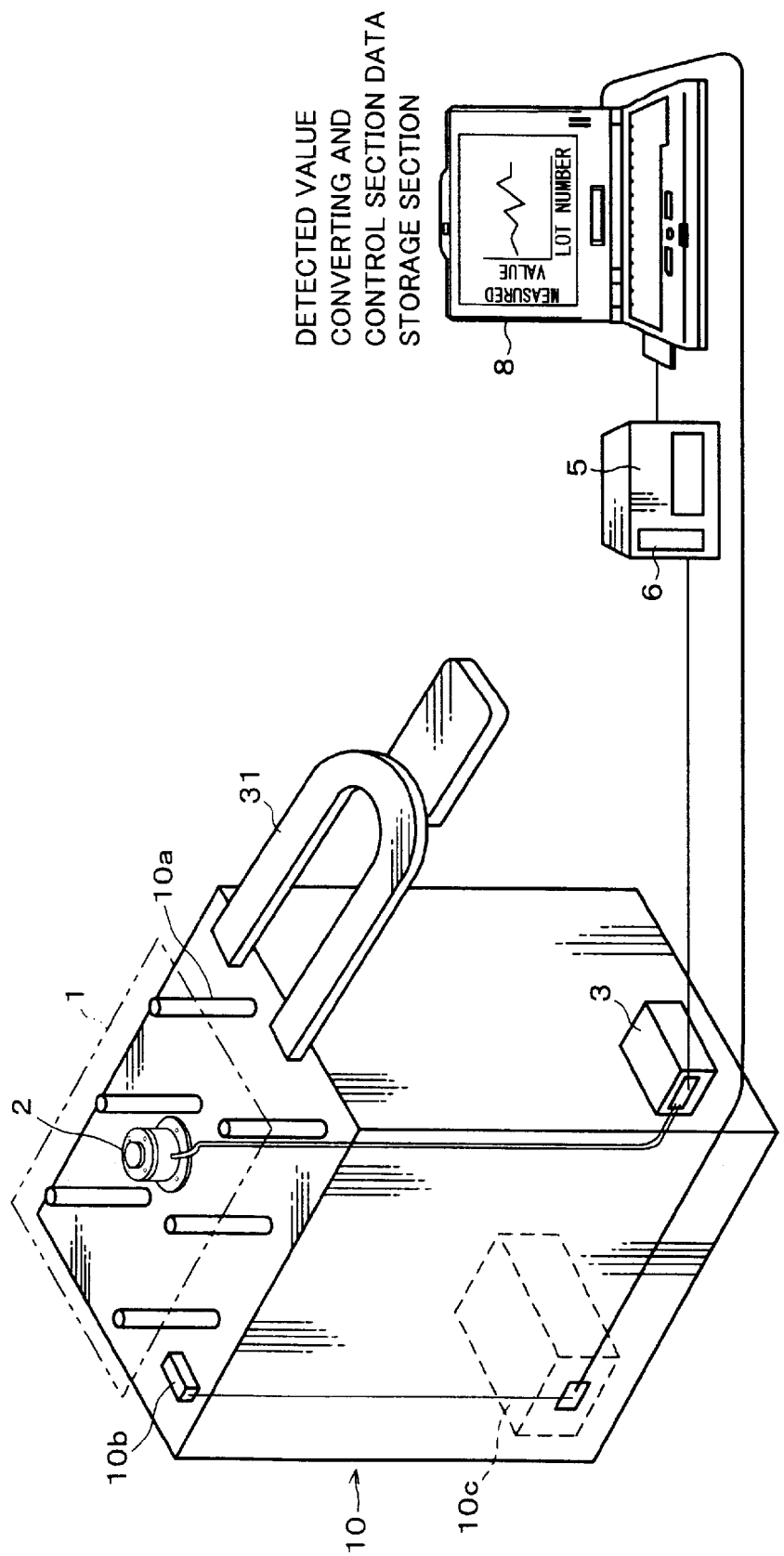
FIG. 20 is a schematic diagram showing a configuration of a sheet resistance meter mounted below a transport stage in a photo line process which immediately follows a film deposition process.
Figure 21:
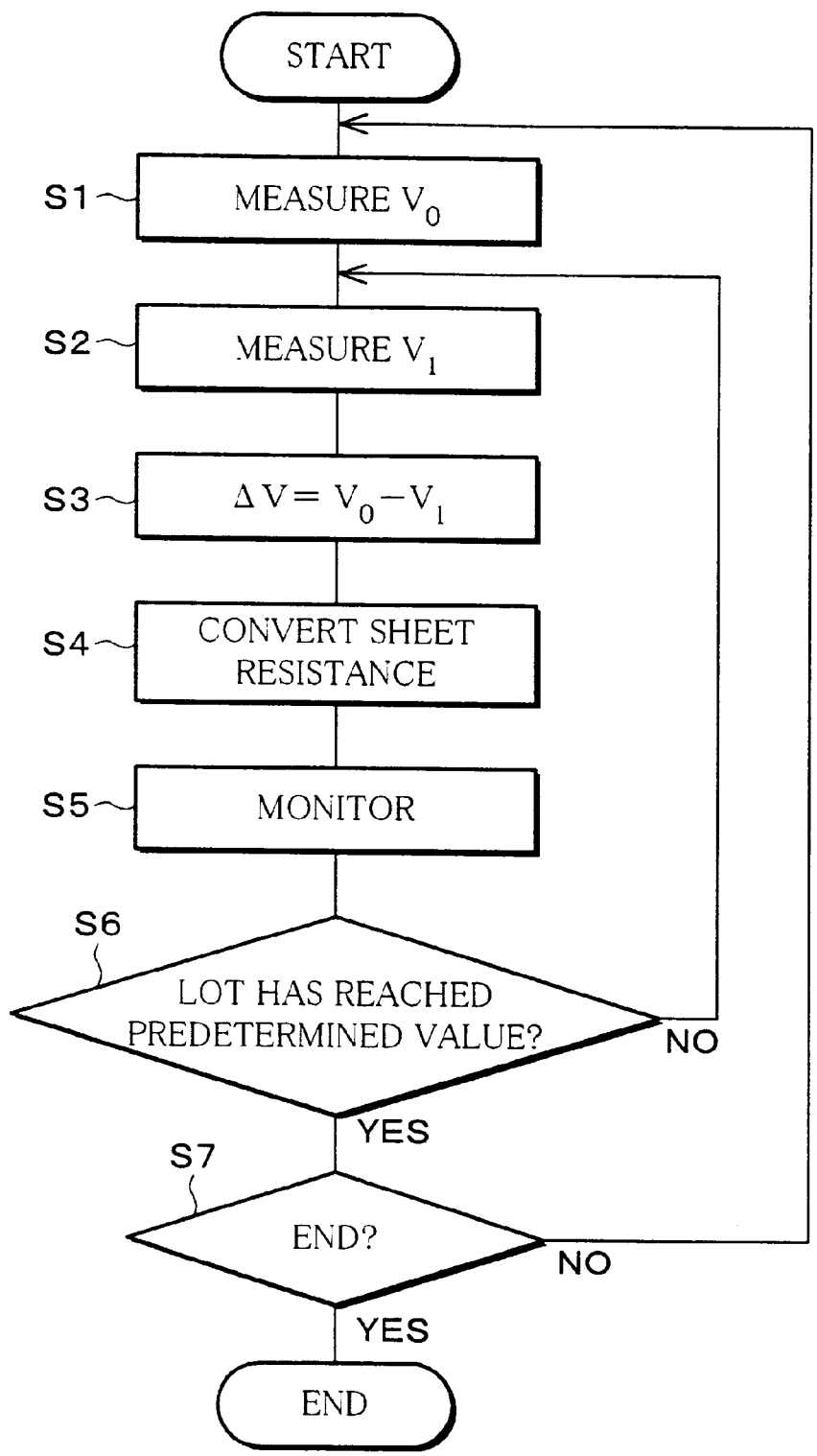
FIG. 21 is a flow diagram showing steps to measure the sheet resistance with the sheet resistance meter according to a method of manufacturing electronic components of the present invention.

Under these circumstances, for example, as shown in FIG. 20, the sheet resistance meter of the present invention is provided on a support table 10 which is disposed below a transport stage used in a photo line following the film formation process. The provision of the sheet resistance meter in the manufacturing line enables monitoring of the sheet resistance without removing the semiconductor wafer 1 from the manufacturing line. When it turns out that there is an abnormality in the sheet resistance, the sheet resistance meter quickly feeds an alarm signal to the CIM process management system (not shown). Electronic components with a thin film 1a are thus manufactured in a stable manner according to the process flow management represented by the flow chart of FIG. 21.

The support table 10 has substrate support pins 10a which support the semiconductor wafer 1. The support table 10 also has a substrate detecting sensor 10b on its top and an internal controlling section 10c, such as a micro computer, which controls the substrate detecting sensor 10b. The controlling section 10c is adapted to feed detected results to the control device 8.

A method of manufacturing electronic components will be explained below according to the flow chart. The voltage is measured ($V=V_0$) first when there is no work object (the semiconductor wafer 1, i.e., the substrate to be measured) in the manufacturing line (step 1; hereinafter, step will be simply written as "S"). Subsequently, the voltage is measured ($V=V_1$) when there is a work object (S2). Here, the sheet resistances of individual semiconductor wafers 1 moving along the manufacturing line are measured separately. That is, the film forming conditions are set to initial values for each lot.

A difference between $V_0$ and $V_1$ ($=\Delta V$) is then calculated (S3). The measured value of the sheet resistance is converted according to $\Delta V$ (S4). The converted value of the sheet resistance obtained in S4 is displayed on a monitor of the control device 8 and stored (S5). Results of the measurement are fed to the CIM process management system.

Then, either the controlling section 10c or the control device 8 determines whether or not conversion has been done on the values of the sheet resistances for the predetermined number of lots of semiconductor wafers 1 (S6). Here, a single lot includes twenty semiconductor wafers, for example. If it is determined in S6 that conversion has not been done on the values of the sheet resistances for the predetermined number of lots, the operation proceeds to S2 where the values of the sheet resistances are obtained from the remaining semiconductor wafers 1.

Meanwhile, if it is determined in S6 that conversion has been done on the values of the sheet resistances for the predetermined number of lots, the operation proceeds to S7 where it is determined whether or not the detection of the sheet resistances of the semiconductor wafers 1 in the manufacturing line is to be discontinued. If it is determined in S7 that the detection is to be continued, the operation proceeds to S1 where the sheet resistances of semiconductor wafers 1 of a new lot are measured. In contrast, if it is determined in S7 that the detection is to be discontinued, the operation ends here.

Results of these procedures show the detected voltage value right after measurement differs from that after 24 hours ($\Delta V$) by 0.027 V, a fluctuation ratio of 0.89%, and substantially identical detected voltage values over a long period of time which are free from adverse effects from drift.

Further, as mentioned above, it was discovered that by forming the capacitor C1 for use in sensitivity adjustment and the resistance R1 included in the resonant circuit from a material which imparts extremely precise temperature properties, the voltage shows a restrained drift in the resonant circuit.

In the above operation, the film forming conditions were set to initial values for each lot. Alternatively, they may be set to initial values for every predetermined period of time, for example. In the event, the initialization is skipped, if there is a work object when the initialization should be done after the predetermined period has elapsed. The film forming conditions are initialized after the predetermined period has elapsed again.

As described above, using the sheet resistance meter of the present invention in the manufacture of electronic components, the electronic components (here, the semiconductor wafers 1) are manufactured with a greatly improved efficiency. Further, when it is determined that the semiconductor wafer 1 has a deficiency, that is, the thin film 1a formed on the semiconductor wafer 1 has a deficiency, the trouble can be brought under control quickly through correction.

For these reasons, according to this method, the yield and throughput can be improved in the manufacture of the semiconductor wafer 1. Responsible personnel can monitor the formation of the thin film 1a for sudden abnormalities and time-dependent variations on the monitor 8a of the control device 8, and easily observe conditions of the semiconductor wafer 1 in the manufacturing line.

Therefore, according to the method, the sheet resistance is measurable while providing protection to the thin film 1a formed on the semiconductor wafer 1 against scratches and other kinds of damage. The quality of films with a wide range of resistance, from Ta and other low resistance films to ITO and other high resistance films, can be readily monitored and controlled without removing the semiconductor wafer 1 from the manufacturing line. Therefore, according to the method, every thin film can be inspected, which obviates sample inspections, in which some semiconductor wafer 1 are selectively inspected.

Therefore, according to the method, a high precision, in-line inspection system be established for the manufacture of the semiconductor wafer 1 to quickly respond to the occurrence of a deficiency in the semiconductor wafer 1 in the manufacturing line. As a result, it is better ensured that thin films 1a are formed on semiconductor wafers with invariable characteristics in a more stable manner.

Figure 22A:
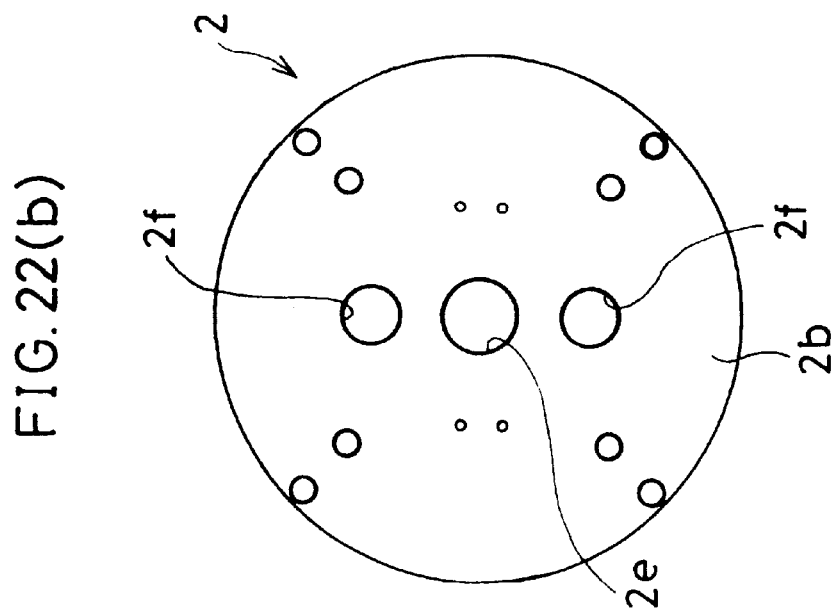
FIGS. 22(a) to 22(c) illustrate a container of a different shape to house the sheet resistance meter, FIGS. 22(a) to 22(c) being a top, bottom, and cross-sectional view of the container respectively.
Figure 22B:
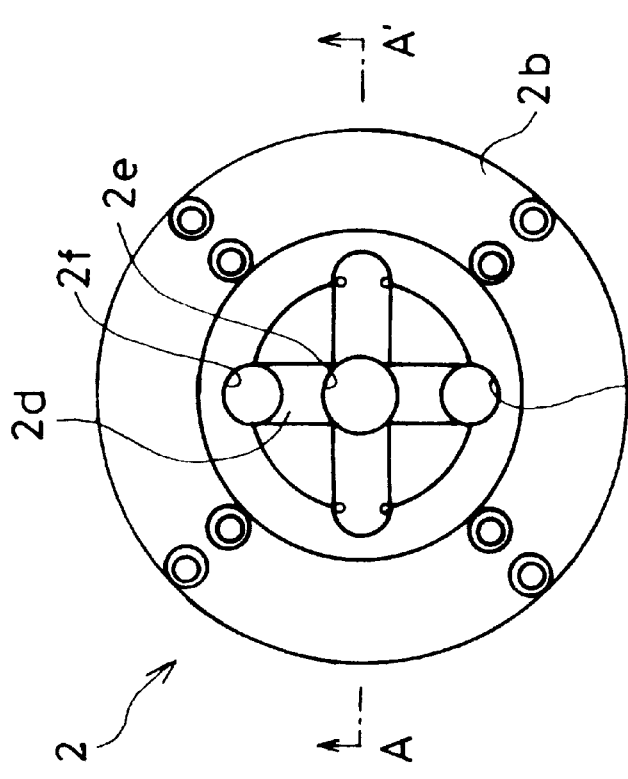
Figure 22C:
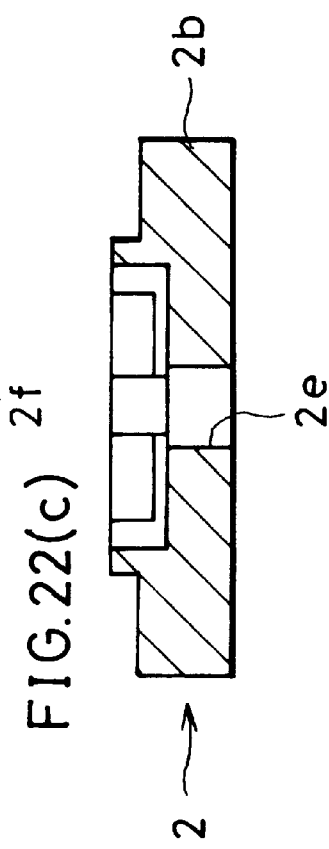
Figure 23:
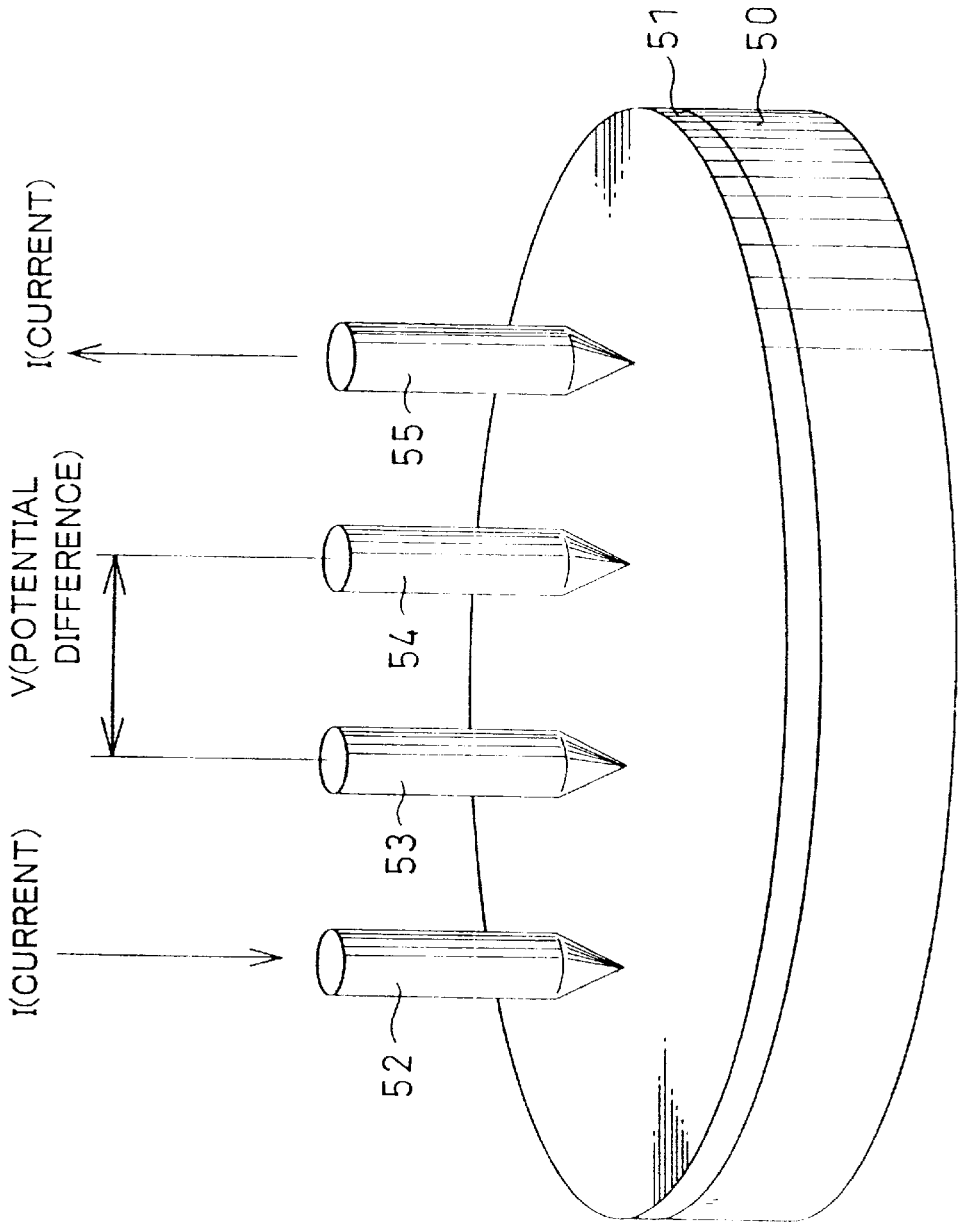
FIG. 23 is a schematic perspective view illustrating a conventional four probe technique to measure a sheet resistance.
Figure 24:
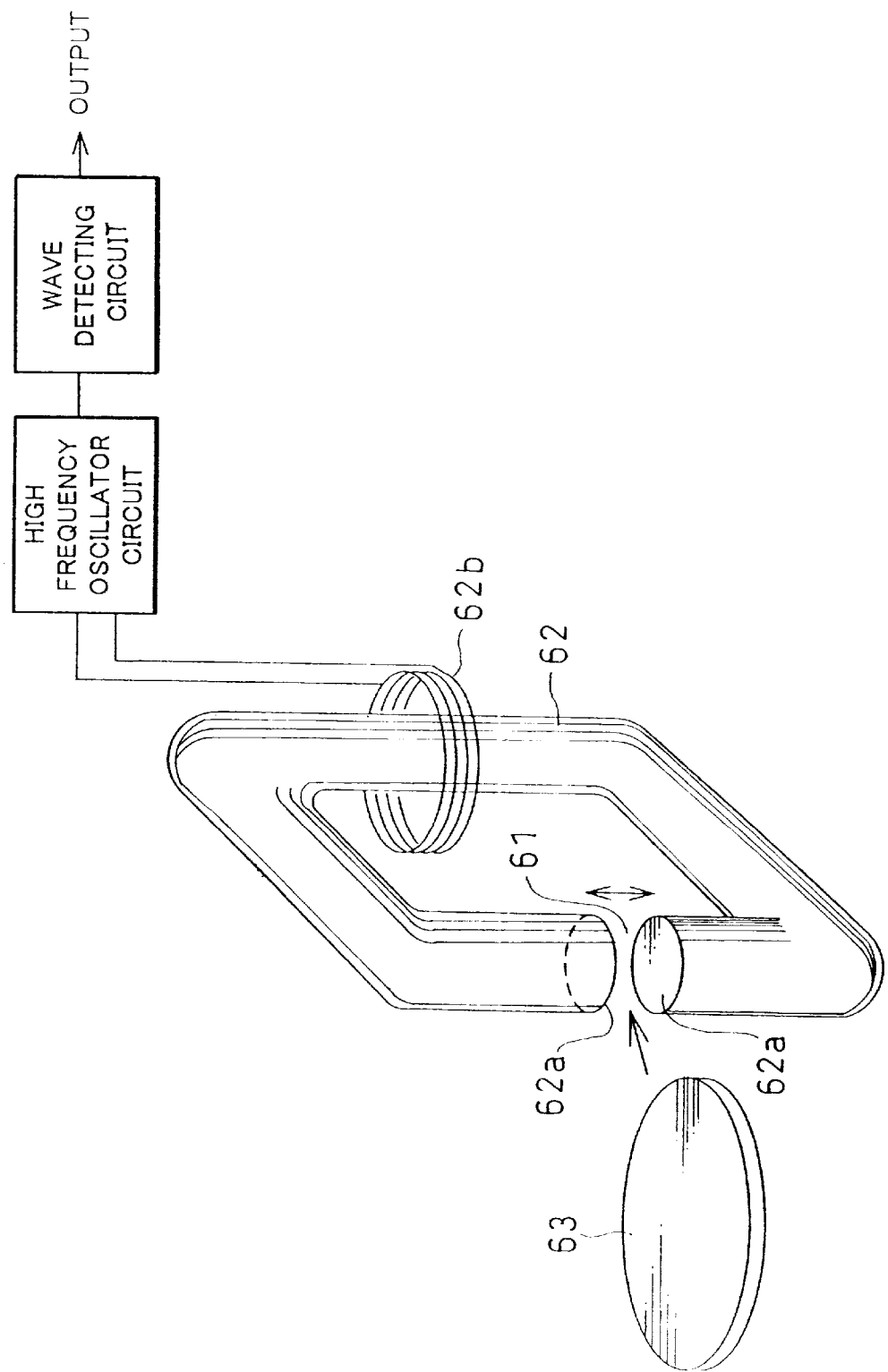
FIG. 24 is a schematic diagram showing a configuration to measure a sheet resistance according to a conventional double-sided eddy current scheme.
Figure 25:
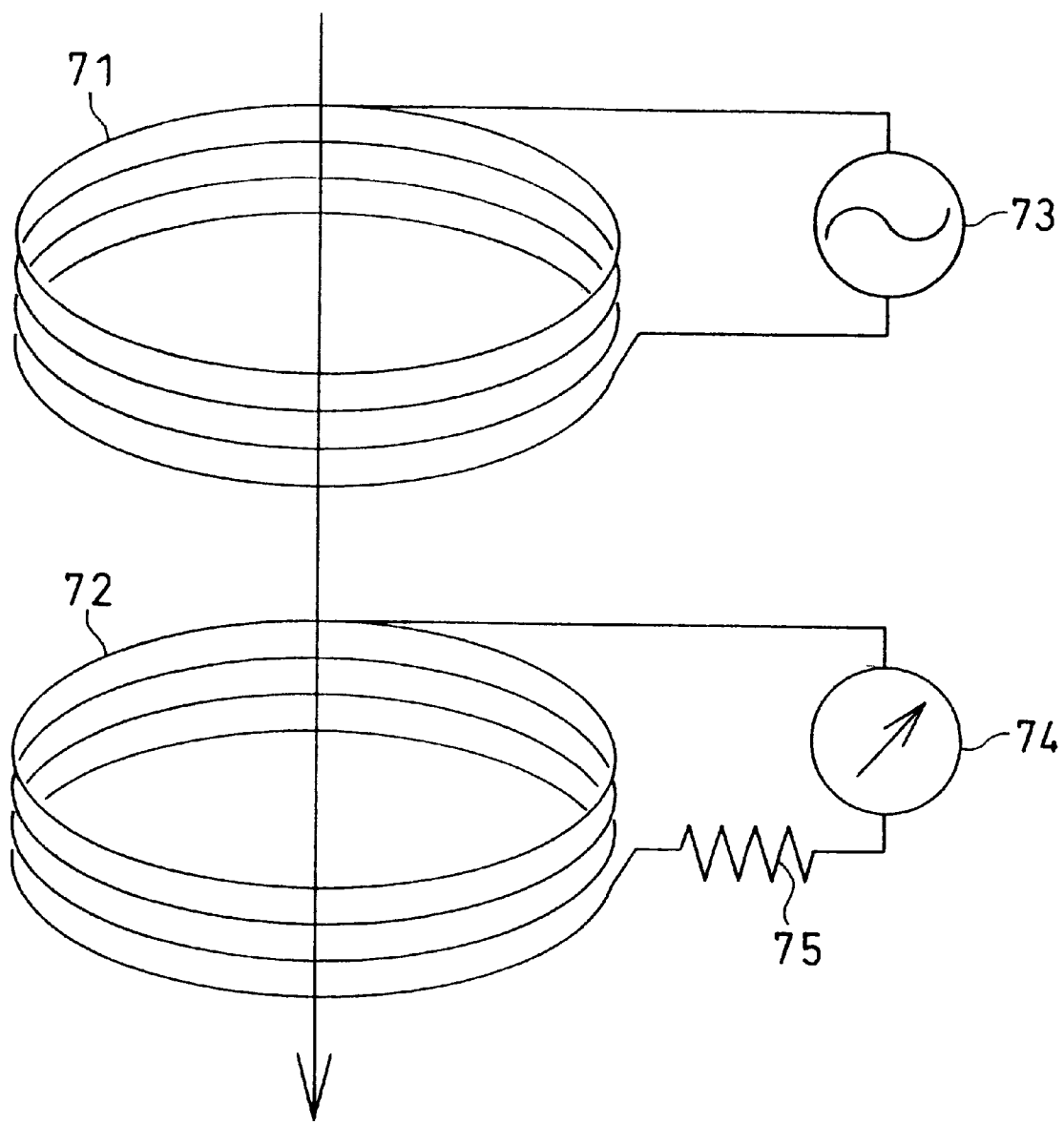
FIG. 25 illustrates the operating principle of an eddy current scheme to measure a sheet resistance.
Figure 26:
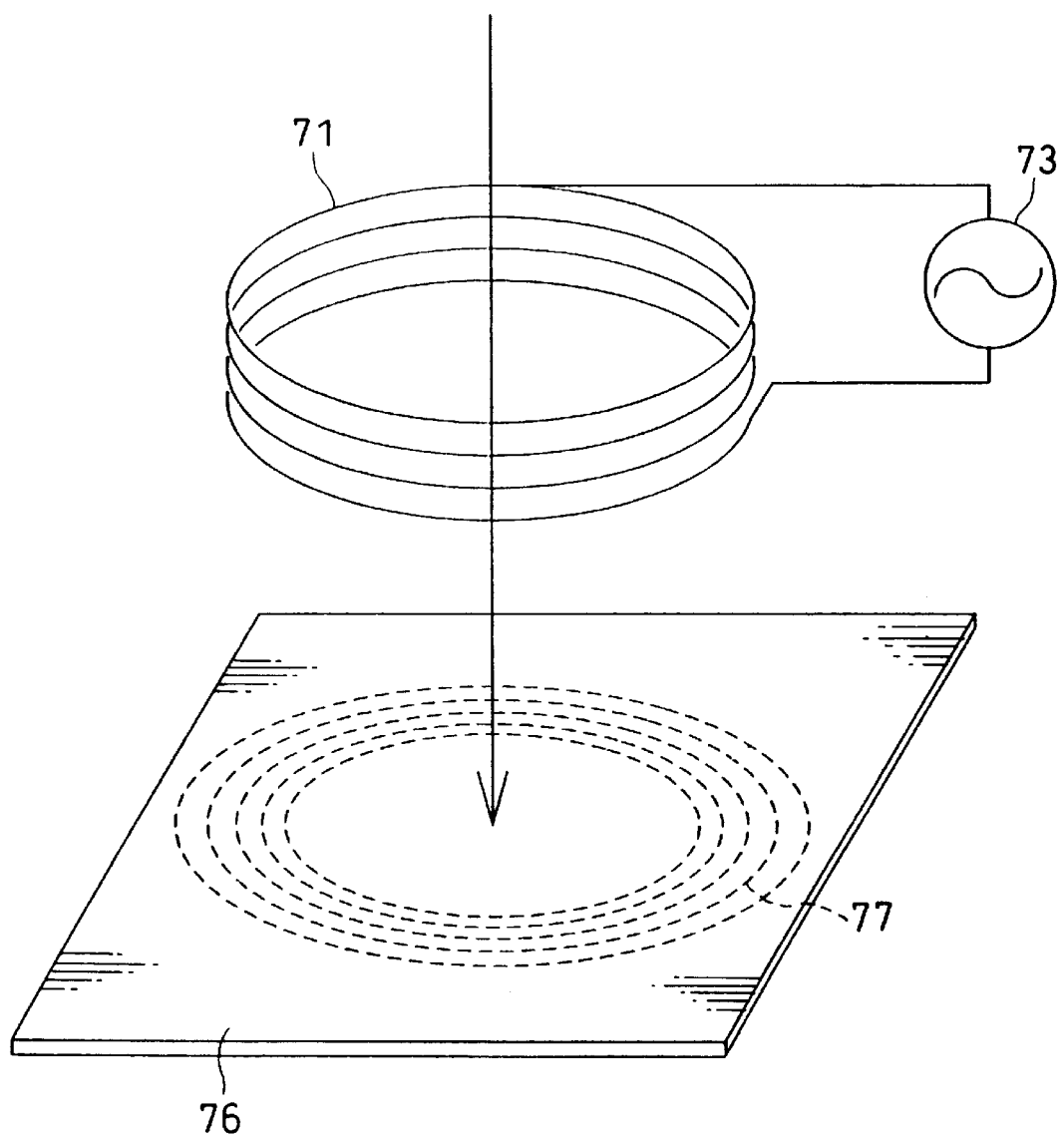
FIG. 26 illustrates the operating principle of an eddy current scheme to measure a sheet resistance.

In the description so far, the temperature controlling section was constituted by a groove section 2d, a primary air port 2e, a pair of auxiliary air ports 2f, and a pair of side air ports 2g as an example. Alternatively, for example, as shown in FIG. 22, the side air ports 2g may be omitted.

In the description so far, the coil 2a was coreless as an example. Alternatively, for example, a columnar core made of ferrite or another material may be inserted in the coil 2a.

As described above, a sheet resistance meter of the present invention is a sheet resistance meter for measuring the sheet resistance of a thin film formed on a substrate, and includes:

a sensor head including a coil which produces a magnetic field to induce eddy currents in the thin film, so that lines of a magnetic force exerted by the magnetic field extend on one side of the substrate;

a sheet resistance detecting section, having a resistor for use in voltage detection, for detecting the sheet resistance of the thin film according to a variation of the magnetic field caused by the eddy currents;

a capacitor for achieving resonance with the coil; and a temperature controlling section which controls a temperature of the coil.

In the arrangement, the provision of the capacitor which achieves resonance with the coil enables the production of a strong magnetic field, and allows the magnetic field to induce strong eddy currents in the thin film.

In this arrangement, the eddy currents dissipate as Joule heat, and the impedance of the coil varies according to the eddy current loss. Hence, the voltage across the resistor for use in voltage detection changes depending on the variation of the impedance. The sheet resistance detecting section detects the sheet resistance of the thin film based on the change in the voltage.

Further, in this arrangement, the sensor head is positioned so that the lines of a magnetic force exerted by the magnetic field extend on one side of the substrate. When compared with a conventional scheme, the arrangement allows more versatility in the measurement using the sensor head, and readily incorporated in a thin film forming step in the manufacture of an electronic component or subsequent to such a thin film forming step, for example.

Further, in the arrangement, a temperature controlling section is provided to control the temperature of the coil. Therefore, by the temperature controlling section controlling the temperature of the coil at a constant value, for example, temperature fluctuations cause only a restrained drift in the voltage value detected by the coil. The sheet resistance meter thereby produces stable detection results in operation, especially, in continuous operation.

In the sheet resistance meter, it is preferred if an amplifier circuit is provided to amplify an output signal from the sensor head before feeding the signal to the sheet resistance detecting section, and its position is determined considering the position of the sensor head.

In the sheet resistance meter, it is preferred if an amplifier circuit is provided to amplify an input signal to the sensor head and an output signal from the sensor head before feeding the output signal to the sheet resistance detecting section, and its position is determined considering the position of the sensor head.

Typically, a 8-mm thick robot arm, for example can offer a limited space to install the sheet resistance detecting section, because it also needs to accommodate an amplifier box which houses a substrate detection sensor and other components. A greater distance should be spared to install it between the sensor head and the sheet resistance detecting section.

In addition, the capacitance of the cable which connects the sensor head to the sheet resistance detecting section varies every time the cable moves due to an operation of the robot arm. Also, the sheet resistance meter is susceptible to external noise, which obstructs stable measurement. However, the foregoing arrangement allows the amplifier circuit to be installed, for example, in the amplifier box of the robot arm, and thereby protects the output signal from amplifier circuit from external adverse effects, enabling stable detection.

In the foregoing sheet resistance meter, the capacitor and the resistor for use in voltage detection may be provided in the amplifier circuit. In such an arrangement, the provision of the capacitor and the resistor for use in voltage detection in the amplifier circuit allows the capacitor and the resistor for use in voltage detection to be integrated in the sensor head, which saves labor which would be otherwise put in the adjustment of the capacitor and the resistor for use in voltage detection every time the sensor head is replaced. The sheet resistance meter is thus manufactured with enhanced stability.

In the foregoing sheet resistance meter, it is preferred if the amplifier circuit is provided close to the sensor head. With the arrangement, the provision of the amplifier circuit close to the sensor head further reduces adverse effects from external noise in the detection of the sheet resistance.

In the foregoing sheet resistance meter, the capacitor and the resistor for use in voltage detection may be provided in the sensor head. Typically, the capacitor needs to be replaced every time sensitivity is changed. Also, fluctuations of the stray capacitance of the cable send adverse effects on sensitivity adjustment in some cases. However, the arrangement reduces adverse effects of twisted cables and external noise and stabilizes the manufacture of sheet resistance meters. The arrangement is advantageous in improvement on sensitivity adjustment, operability, and manufacturability of sensor heads.

In the sheet resistance meter, it is preferred if the capacitor and the resistor for use in voltage detection show restrained variations in capacitance and resistance respectively to temperature rises.

With the arrangement, the use of a capacitor and a resistor for use in voltage detection with good temperature characteristics, which are in a resonant state with the coil, reduces drift in voltage when the sheet resistance meter operates continuously. The capacitor preferably has a capacitance which varies 0 ppm/° C. to 70 ppm/° C. at temperatures from −30° C. to +85° C. The resistor for use in voltage detection preferably has a capacitance which varies ±2.5 ppm/° C. at temperatures from −55° C. to +85° C.

In the sheet resistance meter, it is preferred if a calculation section is further provided to calculate a sheet resistance from a detected voltage value which is equivalent to an eddy current loss, based on a curvilinear approximation which is representative of a correlation between the detected voltage value and a sheet resistance value obtained by a four probe technique.

The detected voltage values exhibit a positive correlation with the sheet resistance values obtained by a four probe technique. Conventionally, sensitivity was adjusted only where the correlation shows linearity. Therefore, detected resistance values were adjustable only when they are in a limited range. Besides, a different conversion equation was used for each material constituting the thin film, and every time the material of the thin film is changed, performance decreased due to increased workloads in arrangement sample management and an increased number of conversion equations. For example, a straight line could be drawn from about 3 Ω/□ to about 3.5 Ω/□ from the correlation data for a Ta gate film in the liquid crystal panel manufacturing processes. However, as the resistance value exceeds 6 Ω/□, the data does not show linearity any longer, and the precision in detection drops by ±19%.

In contrast, with the arrangement, A calculation section is provided to calculate the correlation between the voltage values equivalent to eddy current losses and the sheet resistance values obtained by a four probe technique based on curvilinear approximation, for example, logarithmic approximation. Accordingly, at resistance values exceeding 6 Ω/□, the precision in detection falls within, for example, ±8%, the detection range becomes four times as wide, and the method becomes more adaptable to materials for the thin film.

In the foregoing sheet resistance meter, it is preferred if the sensor head has a main body which houses the coil, and the main body has an air duct port as the temperature controlling section. With the arrangement, the provision of the air duct port prevents the coil, which receives electric power with a frequency as high as a few hundred kilohertz or even higher, from becoming excessively hot during continuous operation, and thereby reduces the drift in detected voltage values derived from the detection signals supplied by the sensor head due to rising temperature. The detect of the sheet resistance is thus stabilized.

Further, the sensor head incorporating the arrangement produces better results (stability in measurement) when it is located in the constant gas flow made by an HEPA (temperature monitoring and controlling device which produces a gas flow of constant temperature at a fixed rate) or another temperature controlling section to monitor and control temperature (25±1° C.) especially in a clean room in a liquid crystal panel or semiconductor manufacturing process.

In the foregoing sheet resistance meter, it is preferred if an adjusting section is provided to adjust the distance between the thin film and the sensor head. With the arrangement, the provision of the adjusting section facilitates sensitivity adjustment or optimization when the material of the thin film is changed, because there is an optimum distance (measuring height) between the sensor head and the thin film where sensitivity is highest in the detection of the sheet resistance of a thin film.

As described above, a method of manufacturing electronic components of the present invention is a method of manufacturing electronic components including the step of forming a thin film on a substrate, using a thin film forming device, and such that the sheet resistance of the thin film is measured using the foregoing sheet resistance meter, and the step of forming a thin film is controlled based on the measurement.

With the method, the sheet resistance of a thin film on a substrate can be always detected in a stable manner, using the sheet resistance meter. The thin film forming step can be controlled quickly once an abnormality occurs in the sheet resistance of a formed thin film. Yields are thus improved in the manufacture of electronic components with a gate Ta or other thin films.

In the method of manufacturing electronic components, the sheet resistance meter may be provided in the thin film forming device, for example, in the load lock chamber or downstream along the flow of the thin film formation. With the method, the provision of the sheet resistance meter in the thin film forming device allows the sheet resistance of the thin film formed to be quickly detected right after the formation. The thin film forming step can be controlled quickly once an abnormality occurs in the sheet resistance of a formed thin film. Yields are thus improved in the manufacture of electronic components.

In the foregoing method of manufacturing an electronic component, the sheet resistance meter may be used in a manufacturing process after the step of forming a thin film. With the method, the substrate right after being subjected to a thin film forming step, for example, is as hot as about 80° C., which may affect the detection of the sheet resistance. The provision of the sheet resistance meter in the manufacturing process after the thin film forming step eliminates these adverse effects and ensures the detection of the sheet resistance of the thin film, while speeding up the detection of the sheet resistance to some extent.

The invention being thus described, it will be obvious that the same may be varied in many ways. Such variations are not to be regarded as a departure from the spirit and scope of the invention, and all such modifications as would be obvious to one skilled in the art intended to be included within the scope of the following claims.

What is claimed is:

1. A sheet resistance meter, comprising:

a sensor head including a coil which produces a magnetic field to induce eddy currents in a thin film formed on a substrate, so that lines of a magnetic force exerted by the magnetic field extend only on one side of the substrate;

a sheet resistance detecting section connected to the coil and having a resistor for use in voltage detection, wherein the sheet resistance detecting section is effective to detect a sheet resistance of the thin film according to a variation of the magnetic field caused by the eddy currents;

a capacitor, connected to the coil, for achieving resonance with the coil; and a temperature controlling section, provided at the sensor head, for controlling a temperature of the coil.

2. The sheet resistance meter as defined in claim 1, further comprising:

an amplifier circuit connected to the coil and positioned close to the sensor head, the amplifier circuit being effective to amplify an output signal outputted from the coil according to loss of the eddy currents.

3. The sheet resistance meter as defined in claim 1, further comprising:

an amplifier circuit connected to the coil and positioned close to the sensor head, the amplifier circuit being effective to amplify an input signal inputted to the coil, and to amplify an output signal, wherein the output signal is outputted from the coil according to loss of the eddy currents.

4. The sheet resistance meter as defined in claim 2, wherein:

the capacitor and the resistor are provided in the amplifier circuit.

5. The sheet resistance meter as defined in claim 1, wherein:

the capacitor and the resistor are provided in the sensor head.

6. The sheet resistance meter as defined in claim 1, wherein:

the capacitor and the resistor have restrained variations in capacitance and resistance, respectively, in response to temperature fluctuations.

7. The sheet resistance meter as defined in claim 1, further comprising:

a calculation section, connected to the sheet resistance detection section, which calculates a sheet resistance from a detected voltage value which is equivalent to an eddy current loss, based on a curvilinear approximation which is representative of a correlation between the detected voltage value and a sheet resistance value obtained by a four probe technique.

8. The sheet resistance meter as defined in claim 1, wherein:

the sensor head has a main body which houses the coil; and the main body has an air duct port as the temperature controlling section.

9. The sheet resistance meter as defined in claim 8, wherein:

the main body is cylindrical and has a bottom; and the coil is provided to share a common axis with the main body.

10. The sheet resistance meter as defined in claim 9, wherein:

the air duct port is at least bored through the main body to extend parallel to the axis of the coil.

11. The sheet resistance meter as defined in claim 9, wherein:

the air duct port is bored through the main body to extend parallel to a radial direction of the coil.

12. The sheet resistance meter as defined in claim 1, further comprising:

an adjusting section, disposed to support the sensor head, for adjusting a distance between the thin film and the sensor head.

13. The sheet resistance meter as defined in claim 12, wherein:

the adjusting section is adapted to adjust the distance based on a correlation factor obtained from a curvilinear approximation of a sheet resistance calculated from a detected voltage value which is equivalent to an eddy current loss and a sheet resistance value obtained by a four probe technique.

14. The sheet resistance meter as defined in claim 1, further comprising:

an air discharge section as the temperature controlling section.

15. A method of manufacturing an electronic component, comprising the step of forming a thin film on a substrate, using a thin film forming device, wherein:

the sheet resistance of the thin film is measured using the sheet resistance meter as defined in claim 1, and the step of forming a thin film is controlled based on the measurement.

16. The method of manufacturing an electronic component as defined in claim 15, wherein:

the sheet resistance meter is provided in the thin film forming device.

17. The method of manufacturing an electronic component as defined in claim 15, wherein:

the sheet resistance meter is used in a manufacturing process after the step of forming a thin film.

18. The method of manufacturing an electronic component as defined in claim 15, wherein:

the sheet resistance meter is provided on a supporting plane of an arm section which transports the substrate.

19. The method of manufacturing an electronic component as defined in claim 18, wherein:

the sheet resistance meter is provided close to a suction section for attracting and thereby securing the substrate, the suction section being provided on a supporting plane of the arm section.

20. The sheet resistance meter as defined in claim 1, wherein the coil, the resistor for use in voltage detection, and the capacitor are connected to each other in series.

21. The sheet resistance meter as defined in claim 1, wherein said coil is coreless.

22. The sheet resistance meter as defined in claim 1, wherein the sensor head produces the magnetic field so that a center one of respective lines of the magnetic force representing the magnetic field crosses a surface of the thin film at right angles.

23. The sheet resistance meter as defined in claim 1, further comprising a cable for connecting the sheet resistance detecting section to the sensor head, wherein said capacitor is set considering stray capacitance of the cable.

24. The sheet resistance meter as defined in claim 1, wherein said coil is formed from a Litzendraht wire by winding it.

25. The sheet resistance meter as defined in claim 1, wherein said sensor head produces the magnetic field which extends on one side of the thin film.

26. The sheet resistance meter as defined in claim 8, wherein said main body is made of non-magnetic material.

* * * * *